United States Patent
Guillaumet et al.

(10) Patent No.: US 7,235,550 B2
(45) Date of Patent: Jun. 26, 2007

(54) POLYCYCLIC AZAINDOLE COMPOUNDS

(75) Inventors: Gérald Guillaumet, Saint Jean le Blanc (FR); Marie-Claude Viaud, Tours (FR); Hervé Van de Poel, Marmagne (FR); Philippe Delagrange, Issy les Moulineaux (FR); Caroline Bennejean, Charenton le Pont (FR); Pierre Renard, Le Chesnay (FR)

(73) Assignee: Les Laboratoires Servier, Courbevoie Cedex (FR)

( * ) Notice: Subject to any disclaimer, the term of this patent is extended or adjusted under 35 U.S.C. 154(b) by 617 days.

(21) Appl. No.: 10/267,303

(22) Filed: Oct. 9, 2002

(65) Prior Publication Data
US 2003/0105087 A1  Jun. 5, 2003

Related U.S. Application Data

(62) Division of application No. 09/689,578, filed on Oct. 12, 2000, now Pat. No. 6,495,543.

(30) Foreign Application Priority Data
Oct. 15, 1999 (FR) .................................. 99 12900

(51) Int. Cl.
A61K 31/535 (2006.01)
C07D 279/36 (2006.01)
C07D 265/34 (2006.01)
C07D 498/02 (2006.01)
C07D 498/12 (2006.01)
C07D 267/02 (2006.01)
C07D 471/00 (2006.01)

(52) U.S. Cl. ............................ 514/230.2; 514/230.5; 544/31; 544/101

(58) Field of Classification Search ............. 514/224.5, 514/230.5, 250, 292, 230.2; 544/32, 101, 544/250, 91, 31; 546/81
See application file for complete search history.

(56) References Cited

U.S. PATENT DOCUMENTS

| | | | | |
|---|---|---|---|---|
| 3,910,901 A | * | 10/1975 | Demerson et al. | 544/32 |
| 3,910,903 A | * | 10/1975 | Demerson et al. | 544/32 |
| 3,912,729 A | * | 10/1975 | Demerson et al. | 544/32 |
| 3,962,236 A | * | 6/1976 | Demerson et al. | 544/101 |
| 4,012,511 A | * | 3/1977 | Demerson et al. | 514/230.2 |
| 4,066,763 A | * | 1/1978 | Demerson et al. | 514/224.5 |
| 5,714,495 A | * | 2/1998 | Viaud et al. | 514/300 |
| 5,919,814 A | * | 7/1999 | Guillaumet et al. | 514/432 |
| 6,057,317 A | * | 5/2000 | Guillaumet et al. | 514/230.2 |
| 6,313,160 B1 | * | 11/2001 | Guillaumet et al. | 514/430 |
| 6,495,543 B1 | * | 12/2002 | Guillaumet et al. | 514/214.01 |
| 6,667,304 B2 | * | 12/2003 | Guillaumet et al. | 514/214.01 |
| 2004/0058939 A1 | * | 3/2004 | Alvarez et al. | 514/267 |

FOREIGN PATENT DOCUMENTS

WO     94/07859    * 4/1994

OTHER PUBLICATIONS

Van de Poel et. al., "Synthesis of . . . 2H-pyrido[2',3':4,5] yrrolo[2,1-b][1,3]oxazine derivatives . . . " Tetrahedron Letters, 2002, vol. 43, No. 7, pp. 1205-1208.*

* cited by examiner

*Primary Examiner*—James O. Wilson
*Assistant Examiner*—Tamthom N. Truong
(74) *Attorney, Agent, or Firm*—Hueschen and Sage

(57) ABSTRACT

The invention relates to compounds of formula (I):

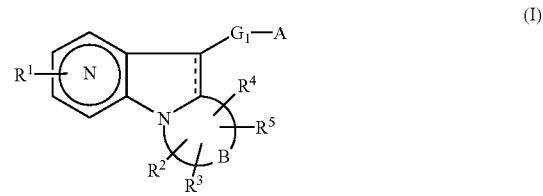

wherein:
$G_1$ represents an alkylene chain as defined in the description,
A represents

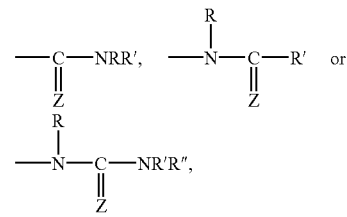

$R^2$ and $R^3$ represent hydrogen, alkyl, alkoxy or hydroxy or together form oxo,
$R^4$ and $R^5$ represent hydrogen,
$R^1$ is as defined in the description,
and medicinal products containing the same which are useful in treating or preventing melatoninergic disorders.

11 Claims, No Drawings

POLYCYCLIC AZAINDOLE COMPOUNDS

The present invention is a division of Ser. No. 09/689,578 filed Oct. 12, 2000 now U.S. Pat. No. 6,495,543.

FIELD OF THE INVENTION

The invention relates to new polycyclic azaindole compounds. The compounds of the present invention are new and have very valuable pharmacological characteristics in respect of melatoninergic receptors.

DESCRIPTION OF THE PRIOR ART

The prior art describes polycyclic azaindole compounds for use in synthesis (Heterocycles, 41 (9), 1995, pp. 1987-98; Tetrahedron Letters, 26 (10), 1985, pp. 1295-6) or as anti-tumour and antiviral agents (Tetrahedron, 50 (13), 1994, pp. 3987-92).

BACKGROUND OF THE INVENTION

Numerous studies in the last ten years have demonstrated the key role of melatonin (N-acetyl-5-methoxytryptamine) in many physiopathological phenomena and in the control of the circadian rhythm. Its half-like is quite short, however, owing to the fact that it is rapidly metabolised. Great interest therefore lies in the possibility of providing the clinician with melatonin analogues that are metabolically more stable, have an agonist or antagonist character and that may be expected to have a therapeutic effect that is superior to that of the hormone itself.

In addition to their beneficial action on circadian rhythm disorders (J. Neurosurg. 1985, 63, pp. 321-341) and sleep disorders (Psychopharmacology, 1990, 100, pp. 222-226), ligands of the melatoninergic system have valuable pharmacological properties in respect of the central nervous system, especially anxiolytic and antipsychotic properties (Neuropharmacology of Pineal Secretions, 1990, 8 (3-4), pp. 264-272) and analgesic properties (Pharmacopsychiat., 1987, 20, pp. 222-223) as well as for the treatment of Parkinson's disease (J. Neurosurg. 1985, 63, pp. 321-341) and Alzheimer's disease (Brain Research, 1990, 528 pp. 170-174). Those compounds have also demonstrated activity in relation to certain cancers (Melatonin—Clinical Perspectives, Oxford University Press, 1988, pp. 164-165), ovulation (Science 1987, 227, pp. 714-720), diabetes (Clinical Endocrinology, 1986, 24, pp. 359-364), and in the treatment of obesity (International Journal of Eating Disorders, 1996, 20 (4), pp. 443-446).

Those various effects are exerted via the intermediary of specific melatonin receptors. Molecular biology studies have demonstrated the existence of a number of receptor subtypes that are capable of binding that hormone (Trends Pharmacol. Sci., 1995, 16, p 50; WO 97.04094). It has been possible, for various species, including mammals, for some of those receptors to be located and characterised. In order to be able to understand the physiological functions of those receptors better, it is of great advantage to have available specific ligands. Moreover, such compounds, by interacting selectively with one or other of those receptors, may be excellent medicaments for the clinician in the treatment of pathologies associated with the melatoninergic system, some of which have been mentioned above.

In addition to the fact that the compounds of the present invention are new, they show very strong affinity for melatonin receptors and/or selectivity for one or other of the melatoninergic binding sites.

DETAILED DESCRIPTION OF THE INVENTION

More especially, the present invention relates to compounds of formula (I):

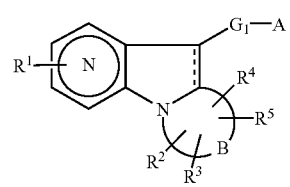

(I)

wherein:

the symbol

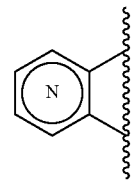

represents the grouping

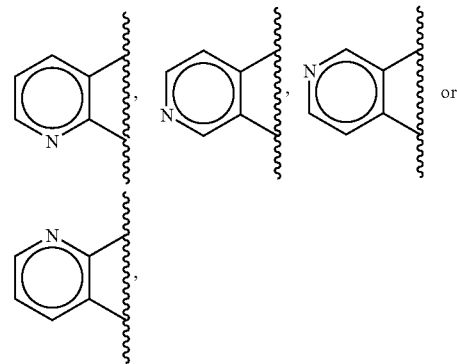

$R^1$ represents a halogen atom or a group —R, —OR, —S(O)$_n$R, —NRR',

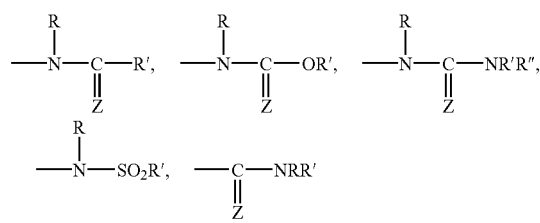

or —SO$_2$NRR' (wherein n is 0, 1 or 2, Z represents a sulphur or oxygen atom, and R, R' and R", which may be identical or different, represent a hydrogen atom or an unsubstituted or substituted linear or branched (C$_1$-C$_6$) alkyl group, an unsubstituted or substituted linear or branched (C$_2$-C$_6$)alkenyl group, an unsubstituted or substituted linear or branched $(C_2-C_6)$alkynyl group, an unsubstituted or substituted $(C_3-C_8)$-cycloalkyl group, an unsubstituted or substituted $(C_3-C_8)$cycloalkyl-$(C_1-C_6)$ alkyl group in which the alkyl moiety is linear or branched, an aryl group, an aryl-$(C_1-C_6)$alkyl group in which the alkyl moiety is linear or branched, a heteroaryl group or a heteroaryl-$(C_1-C_6)$alkyl group in which the alkyl moiety is linear or branched, it also being possible for (R and R') and (R' and R") to form together with the nitrogen atom carrying them a morpholinyl, piperidinyl, piperazinyl or pyrrolidinyl group, those groups being unsubstituted or substituted), $G_1$ represents an alkylene chain having from 1 to 4 carbon atoms, optionally substituted by a group R, OR, COR or COOR (wherein R is as defined hereinbefore), or $G_1$ represents an alkylene chain having from 1 to 4 carbon atoms in which one of $CH_2$ group can be replaced by a cycloalkylene $(C_3-C_8)$ group, A represents a group

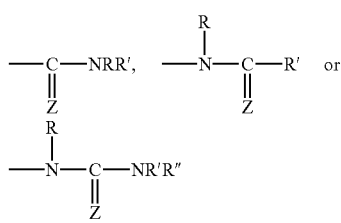

wherein R, R', R" and Z are as defined hereinbefore,

B forms with the nitrogen atom and the carbon atom to which it is attached a ring having from 5 to 8 ring members, which may contain one or more unsaturated bonds and may contain, in addition to the nitrogen atom, an additional hetero atom selected from oxygen, sulphur and nitrogen.

$R^2$ and $R^3$, which may be identical or different, represent a hydrogen atom or a linear or branched $(C_1-C_6)$alkyl group, a linear or branched $(C_1-C_6)$alkoxy group or a hydroxy group, or $R^2$ and $R^3$ together form an oxo group, $R^4$ and $R^5$ represent a hydrogen atom or form together with two adjacent atoms of the B ring carrying them a group selected from aryl and heteroaryl, the symbol ----- means that the bond may be single or double, with the proviso that the valence of the atoms is respected, it being understood that:

the term "substituted" applied to the terms "alkyl", "alkenyl", "alkynyl", "cycloalkyl", "morpholinyl", "piperidinyl", "piperazinyl" and "pyrrolidinyl" means that those groups may be substituted by one or more groups selected from hydroxy, oxo, alkoxy, alkyl, polyhaloalkyl, and halogen atoms, the term "substituted" applied to the term "cycloalkylalkyl" means that the cyclic moiety of the group is substituted by one or more groups selected from hydroxy, oxo, alkoxy, alkyl, polyhaloalkyl, and halogen atoms, "aryl" is understood to mean a phenyl, naphthyl or biphenyl group, those groups being unsubstituted or substituted by one or more identical or different groups selected from hydroxy, alkoxy, alkyl, amino, alkylamino, dialkylamino, nitro, cyano, polyhaloalkyl, formyl, carboxy, alkoxycarbonyl, amido, and halogen atoms, "heteroaryl" is understood to mean a furyl, pyrrolyl, imidazolyl, pyridyl, thienyl, pyrazinyl, benzothienyl, benzofuranyl, indolyl, benzimidazolyl, quinolyl or quinazolinyl group, those groups being unsubstituted or substituted by one or more identical or different groups selected from hydroxy, alkoxy, alkyl, amino, alkylamino, dialkylamino, nitro, cyano, polyhaloalkyl, formyl, carboxy, amido, and halogen atoms, their enantiomers and diastereoisomers, and addition salts thereof with a pharmaceutically acceptable acid or base.

An advantageous variant of the present invention relates to compounds of formula (I):

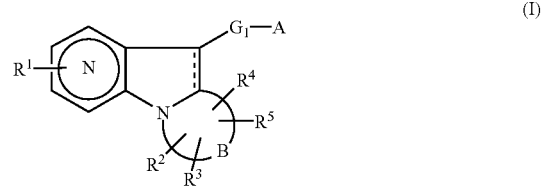

wherein:

the symbol

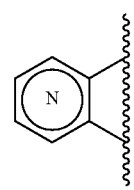

represents the grouping

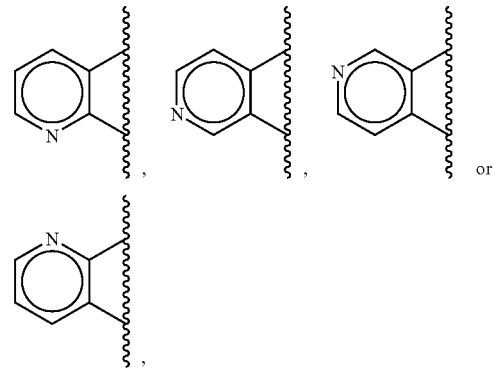

$R^1$ represents a halogen atom or a group —R, —OR, —S(O)$_n$R, —NRR',

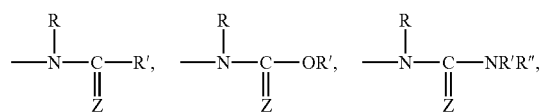

-continued

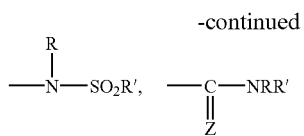

or —SO₂NRR' (wherein n is 0, 1 or 2, Z represents a sulphur or oxygen atom, and R, R' and R", which may be identical or different, represent a hydrogen atom or an unsubstituted or substituted linear or branched ($C_1$-$C_6$) alkyl group, an unsubstituted or substituted linear or branched ($C_2$-$C_6$)alkenyl group, an unsubstituted or substituted linear or branched ($C_2$-$C_6$)alkynyl group, an unsubstituted or substituted ($C_3$-$C_8$)-cycloalkyl group, an unsubstituted or substituted ($C_3$-$C_8$)cycloalkyl-($C_1$-$C_6$) alkyl group in which the alkyl moiety is linear or branched, an aryl group, an aryl-($C_1$-$C_6$)alkyl group in which the alkyl moiety is linear or branched, a heteroaryl group or a heteroaryl-($C_1$-$C_6$)alkyl group in which the alkyl moiety is linear or branched, it also being possible for (R and R') and (R' and R") to form together with the nitrogen atom carrying them a morpholinyl, piperidinyl, piperazinyl or pyrrolidinyl group, those groups being unsubstituted or substituted), $G_1$ represents an alkylene chain having from 1 to 4 carbon atoms, optionally substituted by a group R, OR, COR or COOR (wherein R is as defined hereinbefore).

A represents a group

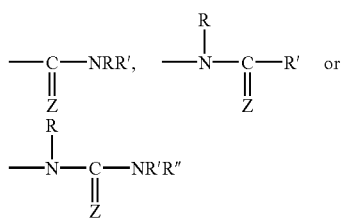

wherein R, R', R" and Z are as defined hereinbefore.

B forms with the nitrogen atom and the carbon atom to which it is attached a ring having from 5 to 8 ring members, which may contain one or more unsaturated bonds and may contain, in addition to the nitrogen atom, an additional hetero atom selected from oxygen, sulphur and nitrogen, $R^2$ and $R^3$, which may be identical or different, represent a hydrogen atom or a linear or branched ($C_1$-$C_6$)alkyl group, a linear or branched ($C_1$-$C_6$)alkoxy group or a hydroxy group, or $R^2$ and $R^3$ together form an oxo group, $R^4$ and $R^5$ represent a hydrogen atom or form together with two adjacent atoms of the B ring carrying them a group selected from aryl and heteroaryl, the symbol ----means that the bond may be single or double, with the proviso that the valence of the atoms is respected, it being understood that:

the term "substituted" applied to the terms "alkyl", "alkenyl", "alkynyl", "cycloalkyl", "morpholinyl", "piperidinyl", "piperazinyl" and "pyrrolidinyl" means that those groups may be substituted by one or more groups selected from hydroxy, oxo, alkoxy, alkyl, polyhaloalkyl, and halogen atoms, the term "substituted" applied to the term "cycloalkylalkyl" means that the cyclic moiety of the group is substituted by one or more groups selected from hydroxy, oxo, alkoxy, alkyl, polyhaloalkyl, and halogen atoms, "aryl" is understood to mean a phenyl, naphthyl or biphenyl group, those groups being unsubstituted or substituted by one or more identical or different groups selected from hydroxy, alkoxy, alkyl, amino, alkylamino, dialkylamino, nitro, cyano, polyhaloalkyl, formyl, carboxy, alkoxycarbonyl, amido, and halogen atoms, "heteroaryl" is understood to mean a furyl, pyrrolyl, imidazolyl, pyridyl, thienyl, pyrazinyl, benzothienyl, benzofuranyl, indolyl, benzimidazolyl, quinolyl or quinazolinyl group, those groups being unsubstituted or substituted by one or more identical or different groups selected from hydroxy, alkoxy, alkyl, amino, alkylamino, dialkylamino, nitro, cyano, polyhaloalkyl, formyl, carboxy, amido, and halogen atoms, their enantiomers and diastereoisomers, and addition salts thereof with a pharmaceutically acceptable acid or base.

An another advantageous variant of the present invention relates to compounds of formula (I):

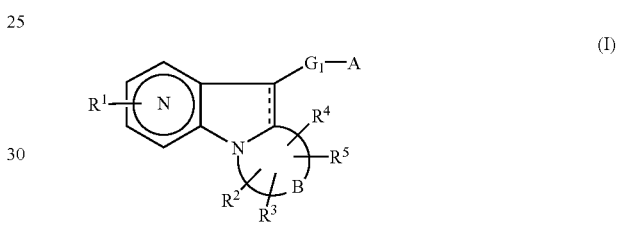

(I)

wherein:
the symbol

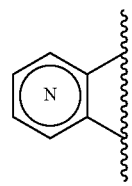

represents the grouping

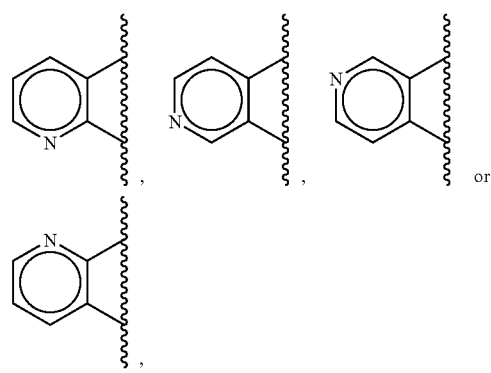

$R^1$ represents a halogen atom or a group —R, —OR, —S(O)$_n$R, —NRR',

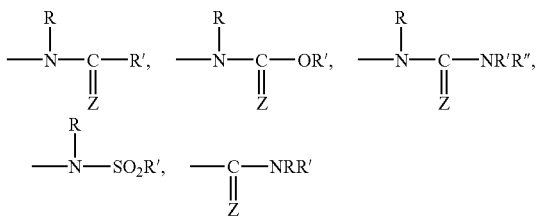

or —SO$_2$NRR' (wherein n is 0, 1 or 2, Z represents a sulphur or oxygen atom, and R, R' and R", which may be identical or different, represent a hydrogen atom or an unsubstituted or substituted linear or branched (C$_1$-C$_6$) alkyl group, an unsubstituted or substituted linear or branched (C$_2$-C$_6$)alkenyl group, an unsubstituted or substituted linear or branched (C$_2$-C$_6$)alkynyl group an unsubstituted or substituted (C$_3$-C$_8$)-cycloalkyl group, an unsubstituted or substituted (C$_3$-C$_8$)cycloalkyl-(C$_1$-C$_6$) alkyl group in which the alkyl moiety is linear or branched, an aryl group, an aryl-(C$_1$-C$_6$)alkyl group in which the alkyl moiety is linear or branched, a heteroaryl group or a heteroaryl-(C$_1$-C$_6$)alkyl group in which the alkyl moiety is linear or branched, it also being possible for (R and R') and (R' and R") to form together with the nitrogen atom carrying them a morpholinyl, piperidinyl, piperazinyl or pyrrolidinyl group, those groups being unsubstituted or substituted), G$_1$ represents an alkylene chain having from 1 to 4 carbon atoms in which one of CH$_2$ group can be replaced by a cycloalkylene (C$_3$-C$_8$) group, A represents a group

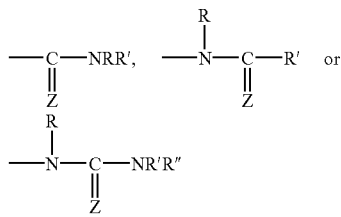

wherein R, R', R" and Z are as defined hereinbefore,

B forms with the nitrogen atom and the carbon atom to which it is attached a ring having from 5 to 8 ring members, which may contain one or more unsaturated bonds and may contain, in addition to the nitrogen atom, an additional hetero atom selected from oxygen, sulphur and nitrogen, R$^2$ and R$^3$, which may be identical or different, represent a hydrogen atom or a linear or branched (C$_1$-C$_6$)alkyl group, a linear or branched (C$_1$-C$_6$)alkoxy group or a hydroxy group, or R$^2$ and R$^3$ together form an oxo group, R$^4$ and R$^5$ represent a hydrogen atom or form together with two adjacent atoms of the B ring carrying them a group selected from aryl and heteroaryl, the symbol ----- means that the bond may be single or double, with the proviso that the valence of the atoms is respected, it being understood that:

the term "substituted" applied to the terms "alkyl", "alkenyl", "alkynyl", "cycloalkyl", "morpholinyl", "piperidinyl", "piperazinyl" and "pyrrolidinyl" means that those groups may be substituted by one or more groups selected from hydroxy, oxo, alkoxy, alkyl, polyhaloalkyl, and halogen atoms.

the term "substituted" applied to the term "cycloalkylalkyl" means that the cyclic moiety of the group is substituted by one or more groups selected from hydroxy, oxo, alkoxy, alkyl, polyhaloalkyl, and halogen atoms, "aryl" is understood to mean a phenyl, naphthyl or biphenyl group, those groups being unsubstituted or substituted by one or more identical or different groups selected from hydroxy, alkoxy, alkyl, amino, alkylamino, dialkylamino, nitro, cyano, polyhaloalkyl, formyl, carboxy, alkoxycarbonyl, amido, and halogen atoms, "heteroaryl" is understood to mean a furyl, pyrrolyl, imidazolyl, pyridyl, thienyl, pyrazinyl, benzothienyl, benzofuranyl, indolyl, benzimidazolyl, quinolyl or quinazolinyl group, those groups being unsubstituted or substituted by one or more identical or different groups selected from hydroxy, alkoxy, alkyl, amino, alkylamino, dialkylamino, nitro, cyano, polyhaloalkyl, formyl, carboxy, amido, and halogen atoms, their enantiomers and diastereoisomers, and addition salts thereof with a pharmaceutically acceptable acid or base.

Among the pharmaceutically acceptable acids there may be mentioned by way of non-limiting example hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, methanesulphonic acid, camphoric acid, etc.

Among the pharmaceutically acceptable bases there may be mentioned by way of non-limiting example sodium hydroxide, potassium hydroxide, triethylamine, tert-butylamine, etc.

The preferred compounds of the invention are the compounds of formula (I) wherein B forms with the nitrogen atom and the carbon atom to which it is attached a pyrrolidine ring, a piperidine ring, a (perhydro)azepine ring (7 ring members), a (perhydro)azocine ring (8 ring members) or a ring containing in addition to the nitrogen atom an oxygen atom, and more preferably a 1,3-(perhydro)oxazine ring.

The preferred groups R$^2$ and R$^3$ of the compounds of formula (I) are the hydrogen atom.

The preferred groups R$^4$ and R$^5$ of the compounds of formula (I) are the hydrogen atom or when R$^4$ and R$^5$, carried by two adjacent atoms of the B ring, form with those two atoms an unsubstituted or substituted phenyl group.

The invention relates more especially to the compounds of formula (I) wherein R$^1$ represents a group OR and more preferably a group OR wherein R represents a hydrogen atom or a linear or branched (C$_1$-C$_6$)alkyl group, such as, for example, methyl, ethyl, propyl, butyl, pentyl, hexyl, isopropyl or tert-butyl.

The preferred group G$_1$ of the compounds of formula (I) is the group (CH$_2$)$_p$ wherein p is 2 or 3 and more preferably 2.

Advantageously, the invention relates to compounds of formula (I) wherein A represents a group NHCOR or CONHR and more especially a group NHCOR or CONHR wherein R represents a linear or branched (C$_1$-C$_6$)alkyl group, such as, for example, methyl, ethyl, propyl, butyl, pentyl, hexyl, isopropyl or tert-butyl, a (C$_3$-C$_8$)cycloalkyl group, such as, for example, cyclopropyl, cyclobutyl, cyclopentyl or cyclohexyl, a (C$_3$-C$_8$)cycloalkyl-(C$_1$-C$_6$)alkyl group in which the alkyl moiety is linear or branched, such as, for example, cyclopropylmethyl, cyclobutylmethyl or cyclohexylmethyl, an aryl group, such as, for example, phenyl, iodophenyl, trifluoromethylphenyl or methoxyphenyl, an aryl-$(C_1$-$C_6)$-alkyl group in which the alkyl moiety is linear or branched, such as, for example, benzyl, or a heteroaryl group, such as, for example, furyl, thienyl, pyrrolyl, pyridyl or indolyl.

The invention relates most especially to the compounds of formula (I) that are

N-[2-(2-methoxy-6H-pyrido[2',3':4,5]pyrrolo[2,1-a]isoindol-11-yl)ethyl]acetamide, N-[2-(2-methoxy-6H-pyrido[2',3':4,5]pyrrolo[2,1-a]isoindol-11-yl)ethyl]-2-furamide, N-[2-(2-methoxy-6H-pyrido[2',3':4,5]pyrrolo[2,1-a]isoindol-11-yl)ethyl]benzamide, N-[2-(3-methoxy-6,7,8,9-tetrahydropyrido[3,2-b]indolizin-5-yl)ethyl]acetamide, N-[2-(2-methoxy-6,7,8,9-tetrahydropyrido[2,3-b]indolizin-10-yl)ethyl]-2-furamide, N-[2-(2-methoxy-6,7,8,9-tetrahydropyrido[2,3-b]indolizin-10-yl)ethyl]acetamide, N-[2-(8-methoxy-3,4-dihydro-2H-pyrido[2',3':4,5]pyrrolo[2,1-b][1,3]oxazin-10-yl)-ethyl]acetamide, N-[2-(8-methoxy-3,4-dihydro-2H-pyrido[2',3':4,5]pyrrolo[2,1-b][1,3]oxazin-10-yl)-ethyl]-2-furamide, N-[2-(10-methoxy-5,6-dihydropyrido[2',3':4,5]pyrrolo[2,1-a]isoquinolin-12-yl)-ethyl]-2-furamide, N-[2-(11-methoxy-6,7-dihydro-5H-pyrido[2',3':4,5]pyrrolo[2,1-a][2]benzazepin-13-yl)ethyl]acetamide, N-[2-(11-methoxy-6,7-dihydro-5H-pyrido[2',3':4,5]pyrrolo[2,1-a][2]benzazepin-13-yl)ethyl]-2-furamide, N-[2-(11-hydroxy-6,7-dihydro-5H-pyrido[2',3':4.5]pyrrolo[2,1-a][2]benzazepin-13-yl)ethyl]-2-furamide.

The enantiomers, diastereoisomers and addition salts with a pharmaceutically acceptable acid or base of the preferred compounds of the invention form an integral part of the invention.

The invention relates also to a process for the preparation of compounds of formula (I), characterised in that there is used as starting material a compound of formula (II):

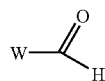
(II)

wherein W represents a radical of formula (III):

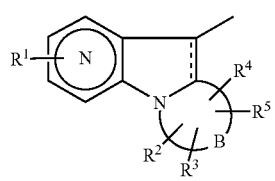
(III)

wherein $R^1$, $R^2$, $R^3$, $R^4$, $R^5$, B, the symbol

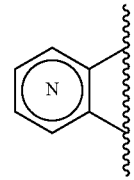

and the symbol ----- are as defined hereinbefore,
which is subjected to
the action of a reducing agent to obtain a compound of formula (IV):

(IV)

wherein W is as defined hereinbefore,
which, after conversion to the corresponding halogen compound, is subjected to the action of a cyanide salt to yield a compound of formula (V):

(V)

wherein W is as defined hereinbefore,
or, in succession, a Wittig reaction and then reduction to obtain a compound of formula (VI):

(VI)

wherein W is as defined hereinbefore, X represents a group CN or COOalk (wherein alk represents an alkyl group) and $G'_1$ represents a chain as defined hereinbefore for $G_1$ having from 2 to 4 carbon atoms, which compounds of formulae (V) and (VI) are hydrolysed in an acidic or basic medium to obtain a compound of formula (VII):

(VII)

wherein W and $G_1$ are as defined hereinbefore,
which is subjected, in the presence of a coupling agent or after conversion to the corresponding acid chloride, to the action of an amine HNRR' wherein R and R' are as defined hereinbefore to yield a compound of formula (I/a) a particular case of the compounds of formula (I):

(I/a)

wherein W, $G_1$, R and R' are as defined hereinbefore,
which compound of formula (I/a), when R and R' simultaneously represent a hydrogen atom, is subjected to the action of NaOBr to yield, after hydrolysis, a compound of formula (VIII):

(VIII)

wherein W and $G_1$ are as defined hereinbefore,
which is subjected to the action of:
an acyl chloride of formula (IX):

(IX)

wherein R is as defined hereinbefore, or the corresponding acid anhydride (mixed or symmetric), to obtain a compound of formula (I/b), a particular case of the compounds of formula (I):

$$W-G_1-NH-\underset{\underset{O}{\|}}{C}-R \quad (I/b)$$

wherein W, $G_1$ and R are as defined hereinbefore.

which compound of formula (I/b) may also be obtained, when $G_1$ represents a chain $(CH_2)_2$, starting from a compound of formula (II) by the action of nitromethane to yield a compound of formula (III'):

$$W-\!\!\!\diagup\!\!\!\!\diagdown\!\!-NO_2 \quad (III')$$

wherein W is as defined hereinbefore, which is subjected to the action of a reducing agent, such as $NaBH_4$, for example, to obtain a compound of formula (IV'):

$$W-\!\!\!\diagup\!\!\!\!\diagdown\!\!-NO_2 \quad (IV')$$

wherein W is as defined hereinbefore.

which is subjected to catalytic hydrogenation to obtain a compound of formula (V'):

$$W-\!\!\!\diagup\!\!\!\!\diagdown\!\!-NH_2 \quad (V')$$

wherein W is as defined hereinbefore, which is subjected to the action of an acid chloride of formula (IX) or the corresponding acid anhydride (mixed or symmetric) to obtain a compound of formula (I/b'), a particular case of the compounds of formula (I/b):

$$W-\!\!\!\diagup\!\!\!\!\diagdown\!\!-NHCOR \quad (I/b')$$

wherein W and R are as defined hereinbefore, or which compound of formula (VIII) is subjected to the action of a compound of formula (X):

$$O\!=\!C\!=\!N-R \quad (X)$$

wherein R is as defined hereinbefore, to yield a compound of formula (I/c), a particular case of the compounds of formula (I):

$$W-G_1-NH-\underset{\underset{O}{\|}}{C}-NH-R \quad (I/c)$$

wherein W, $G_1$ and R are as defined hereinbefore.

which compounds of formulae (I/b) and (I/c) may be subjected to the action of a compound of formula (XI):

$$R_a\text{-}J \quad (XI)$$

wherein $R_a$ can have any of the meanings of R with the exception of the hydrogen atom and J represents a leaving group, such as a halogen atom or a tosyl group.

to yield a compound of formula (I/d), a particular case of the compounds of formula (I):

$$W-G_1-\underset{R_a}{\overset{R_a}{N}}-\underset{\underset{O}{\|}}{C}-Y \quad (I/d)$$

wherein W, $G_1$ and $R_a$ are as defined hereinbefore and Y represents a group R or —NRR' wherein R and R' are as defined hereinbefore, and/or which compounds of formulae (I/a), (I/b), (I/c) and (I/d) may be subjected to the action of a thionisation agent, such as Lawesson's reagent, to yield a compound of formula (I/e), a particular case of the compounds of formula (I):

$$W\text{-}G_1\text{-}T \quad (I/e)$$

wherein W and $G_1$ are as defined hereinbefore and T represents a group $$-\underset{\underset{S}{\|}}{C}-N\!\!\diagup\!\!\overset{R}{\diagdown}\!_{R'} \quad \text{or} \quad -\underset{\underset{}{}}{\overset{R}{N}}-\underset{\underset{S}{\|}}{C}-Y$$

wherein R, R' and Y are as defined hereinbefore.

which compounds (I/a) to (I/e) constitute the totality of the compounds of formula (I) and may be purified according to a conventional purification technique, are converted, if desired, into their addition salts with a pharmaceutically acceptable acid or base, and separated, where appropriate, into their isomers according to a conventional separation technique.

The compounds of formula (III) are either commercial products or are accessible to the person skilled in the art by conventional chemical reactions.

In particular, the compounds of formula (III) may be obtained starting from a compound of formula (XII):

(XII)

wherein $R^1$ and the symbol

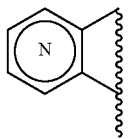

are as defined hereinbefore, which is either a commercial product or is obtained according to a procedure described by G. Guillaumet et al. (Heterocycles, 1999, 50 (2), pp. 1065-1079), which is condensed with a compound of formula (XIII):

Hal-G$_2$-Hal (XIII)

wherein Hal represents a halogen atom and G$_2$ represents a chain containing from 3 to 6 ring members, substituted by the groups R$^2$, R$^3$, R$^4$ and R$^5$ as defined hereinbefore, that may contain one or more unsaturated bonds and optionally contains a hetero atom selected from oxygen, nitrogen and sulphur, to yield a compound of formula (XIV)

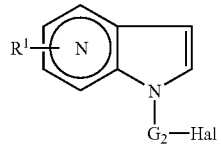
(XIV)

wherein R$^1$, G$_2$, Hal and the symbol

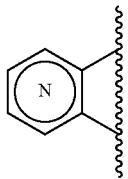

are as defined hereinbefore, which is converted, by the successive action of bromine in tBuOH and then zinc in acetic acid, to a compound of formula (XV):

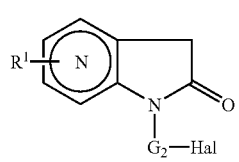
(XV)

wherein R$^1$, G$_2$, Hal and the symbol

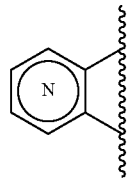

are as defined hereinbefore, or formylated by the action of POCl$_3$ in dimethylformamide (DMF) to yield a compound of formula (XVI):

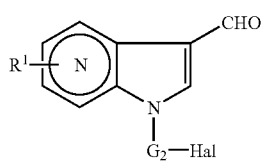
(XVI)

wherein R$^1$, G$_2$ Hal and the symbol

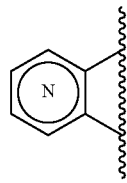

are as defined hereinbefore.

(it also being possible for the compound of formula (XVI) to be obtained starting from a compound of formula (XII), which is subjected in succession to formylation and then to condensation of the compound of formula (XIII)), which compound of formula (XVI) is placed in cyclisation conditions, such as Bu$_3$SnH/AIBN, to yield a compound of formula (III), which compounds of formulae (XIV) and (XV) may also be subjected to cyclisation conditions using, depending upon the case, reagents such as, for example, NaH in DMF or (PPh$_3$)$_4$ Pd, to yield a compound of formula (XVII):

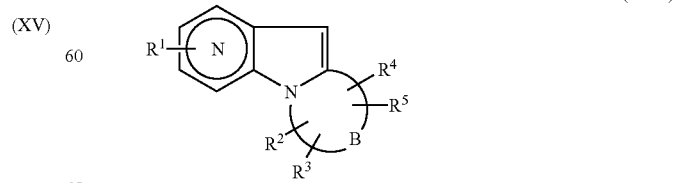
(XVII)

wherein R$^1$, R$^2$, R$^3$, R$^4$, R$^5$, B and the symbol

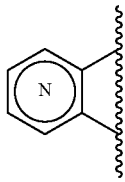

are as defined hereinbefore, which is subjected to formylation conditions, such as POCl$_3$ in DMF, to obtain a compound of formula (III).

The present invention relates also to compounds of formula (XVII) as defined hereinbefore for use as intermediates in the synthesis of compounds of formula (I).

The compounds of the invention and the pharmaceutical compositions containing them have proved to be useful in the treatment of disorders of the melatoninergic system.

Pharmacological study of the compounds of the invention has in fact shown that they are atoxic, have a very high affinity for melatonin receptors and have substantial activities in respect of the central nervous system, and, in particular, therapeutic properties in respect of sleep disorders, anxiolytic, antipsychotic and analgesic properties, as well as properties in respect of microcirculation have been found, enabling it to be established that, the compounds of the invention are useful in the treatment of stress, sleep disorders, anxiety, seasonal affective disorder, cardiovascular pathologies, pathologies of the digestive system, insomnia and fatigue due to jetlag, schizophrenia, panic attacks, melancholia, appetite disorders, obesity, insomnia, psychotic disorders, epilepsy, diabetes, Parkinson's disease, senile dementia, various disorders associated with normal or pathological ageing, migraine, memory loss, Alzheimer's disease, and in cerebral circulation disorders. In another field of activity, it appears that the compounds of the invention can be used in the treatment of sexual dysfunctions, that they have ovulation-inhibiting and immunomodulating properties and are capable of being used in the treatment of cancers.

The compounds will preferably be used in the treatment of seasonal affective disorder, sleep disorders, cardiovascular pathologies, insomnia and fatigue due to jetlag, appetite disorders and obesity.

For example, the compounds will be used in the treatment of seasonal affective disorder and sleep disorders.

The present invention relates also to pharmaceutical compositions comprising at least one compound of formula (I) on its own or in combination with one or more pharmaceutically acceptable excipients.

Among the pharmaceutical compositions according to the invention, there may be mentioned more especially those that are suitable for oral, parenteral, nasal, per- or transcutaneous, rectal, perlingual, ocular or respiratory administration and especially tablets or dragees, sublingual tablets, gelatin capsules, glossettes, lozenges, suppositories, creams, ointments, dermal gels, and drinkable or injectable ampoules.

The dosage varies according to the sex, age and weight of the patient, the route of administration, the nature of the therapeutic indication or any associated treatments, and ranges from 0.01 mg to 1 g per 24 hours in one or more administrations.

The following Examples illustrate the invention but do not limit it in any way. The following Preparations yield synthesis intermediates for use in the preparation of the compounds of the invention.

Preparation 1: 2-(2-Methoxy-6H-pyrido[2',3':4,5] pyrrolo[2,1-a]isoindol-11-yl)-ethylamine Step A:
2-(6-Methoxy-3-nitro-2-pyridinyl)acetonitrile Under argon and in an anhydrous medium, 15 g (97.3 mmol) of 2-methoxy-5-nitropyridine and 17.9 g (107 mmol) of 4-chlorophenoxyacetonitrile are dissolved in 300 ml of anhydrous tetrahydrofuran; the solution is added by transfer to a solution of 24 g (214 mmol) of potassium tert-butylate in 220 ml of anhydrous tetrahydrofuran maintained at a temperature below −10° C. The reaction mixture is stirred for three hours at a temperature of from −10 to −15° C. An aqueous 5% hydrochloric acid solution (170 ml) is added dropwise to the reaction mixture, maintaining the temperature at −10° C. The mixture is extracted with ethyl acetate. After drying over magnesium sulphate and evaporation, the residue is purified by flash chromatography over silica gel (eluant:petroleum ether/ethyl acetate, 2:1). After washing with a petroleum ether/diethyl ether mixture (2:1), the title compound is obtained in the form of a brown product.

Melting point: 116-117° C.

Step B: 5-Methoxy-1H-pyrrolo[3,2-b]pyridine

Under a hydrogen pressure of 45 psi, 17.70 g (91.7 mmol) of the compound obtained in Step A and 2.5 g of palladium-on-carbon suspended in 300 ml of ethanol are stirred for 5 hours at room temperature. After filtration over Celite and evaporation, the residue is purified over silica gel (eluant: petroleum ether/ethyl acetate, 4:1) to yield the title product in the form of a brown solid.

Melting point: 111-112° C.

Step C: 1-(2-Bromobenzyl)-5-methoxy-1H-pyrrolo [3,2-b]pyridine

Under argon and in an anhydrous medium, 590 mg (14.75 mmol) of sodium hydride (60% in oil) are added slowly to a solution of 1.81 g (12.23 mmol) of the compound obtained in Step B in 50 ml of N,N-dimethylformamide at 0° C. After 30 minutes' stirring at room temperature, 2.27 ml (14.75 mmol) of 2-bromobenzyl bromide in 15 ml of N,N-dimethylformamide are added dropwise to the reaction mixture. Stirring is maintained at room temperature under argon for two hours. After hydrolysis and then extraction with ethyl acetate, the organic phase is washed several times with water, dried over magnesium sulphate, concentrated and purified by flash chromatography over silica gel (eluant: petroleum ether/ethyl acetate, 8:2) to yield the title compound in the form of a brown solid.

Melting point: 86-87° C.

Step D: 2-Methoxy-6H-pyrido[2',3':4,5]pyrrolo[2,1-a]isoindole

Under an inert atmosphere, 500 mg (1.57 mmol) of the compound obtained in Step C, 88 mg (78.9 μmol) of tetrakis(triphenylphosphine)palladium(0) and 155 mg (1.57 mmol) of potassium acetate in 15 ml of N,N-dimethylacetamide are heated at 160° C. for 2 hours. After returning to room temperature, the reaction mixture is filtered using a Büchner funnel and then evaporated to dryness. The residue is then hydrolysed and subsequently extracted with ethyl acetate. The organic phase is dried over magnesium sulphate, concentrated and purified by flash chromatography over silica gel (eluant:petroleum ether/ethyl acetate, 8:2) to yield the title compound in the form of a brown solid.

Melting point: 192-193° C.

Step E: 2-Methoxy-6H-pyrido[2',3':4,5]pyrrolo[2,1-a]isoindole-11-carbaldehyde

Under argon and in an anhydrous medium, 291 µl (3.17 mmol) of phosphorus oxychloride are added dropwise to 6 ml of N,N-dimethylformamide maintained at 0° C.: after 15 minutes' stirring, 500 mg (2.11 mmol) of the compound obtained in Step D dissolved in 10 ml of N,N-dimethylformamide are added by transfer. The reaction mixture is stirred for 30 minutes at 0° C. and then for 2 hours at room temperature. The reaction mixture is evaporated to dryness and then taken up in water: the aqueous phase is rendered alkaline with a 6N sodium hydroxide solution and extracted several times with ethyl acetate. The combined organic phases are dried over magnesium sulphate, filtered and evaporated. After washing with a petroleum ether/diethyl ether mixture, the title compound is obtained in the form of a brown solid.

Melting point: 229-230° C.

Step F: 2-Methoxy-11-[2-nitroethenyl]-6H-pyrido[2',3':4,5]pyrrolo[2,9-a]-isoindole 600 mg (2.27 mmol) of the compound obtained in Step E dissolved in 25 ml of nitromethane are heated at 120° C. for 3 hours in the presence of 440 mg (5.67 mmol) of ammonium acetate. After returning to room temperature and evaporation to dryness, the reaction mixture is diluted in dichloromethane and washed with water. After drying over magnesium sulphate, evaporation of the organic phase yields the title compound in the form of a yellow solid.

Melting point: 197-198° C.

Step G: 2-Methoxy-11-(2-nitroethyl)-6H-pyrido[2',3':4,5]pyrrolo[2,1-a]-isoindole Under argon and in an anhydrous medium, 660 mg (2.15 mmol) of the compound obtained in Step F are suspended in 10 ml of isopropanol and 30 ml of chloroform in the presence of 1.5 g of 230-400 mesh silica; 408 mg (10.75 mmol) of sodium borohydride are added slowly. After 30 minutes' stirring at room temperature, acetic acid is added and the reaction mixture is filtered through a glass frit. After removal of the solvents by evaporation, the residue is diluted in dichloromethane and washed with water. The organic phase is then dried over magnesium sulphate, filtered and concentrated to yield the title compound in the form of a yellow solid.

Melting point: 127-128° C.

Step H: 2-(2-Methoxy-6H-pyrido[2',3':4,5]pyrrolo[2,1-a]isoindol-11-yl)-ethylamine Under a hydrogen pressure of 55 psi, 530 mg (1.71 mmol) of the compound obtained in Step G and 210 mg of Raney nickel are stirred in 20 ml of methanol at 60° C. for 15 hours. After returning to room temperature, the reaction mixture is filtered using a Büchner funnel and then evaporated to yield the title amine in the form of a brown oil.

Melting point (oxalate): 149-150° C.

Preparation 2: 2-[2-Methoxy-8-(trifluoromethyl)-6H-pyrido[2',3':4,5]pyrrolo[2,1-a]-isoindol-11-yl] ethylamine The procedure is as for Preparation 1, in Step C replacing 2-bromobenzyl bromide by (4-trifluoromethyl)-2-bromobenzyl bromide.

Preparation 3: 4-(2-Methoxy-6H-pyrido[2',3':4,5]pyrrolo[2,1-a]isoindol-11-yl)-butanoic acid Step A: Ethyl 4-(2-methoxy-6H-pyrido[2',3':4,5]pyrrolo[2,1-a]isoindol-11-yl)-3-butenoate 10.7 mmol of the compound obtained in Step E of Preparation 1 in 20 ml of anhydrous THF are placed in the presence of 1.2 eq of NaH (60% in oil) in 25 ml of anhydrous THF and of 1.2 eq of ethyl 3-(diethoxyphosphoryl)propanoate. The title compound is obtained after 3 hours' stirring at room temperature and gentle refluxing overnight.

Step B: 4-(2-Methoxy-6H-pyrido[2',3':4,5]pyrrolo[2,1-a]isoindol-11-yl)-butanoic acid The ester obtained in Step A is placed in 150 ml of ethanol in the presence of 40 ml of 2N sodium hydroxide solution. The title acid is isolated after stirring at room temperature and then refluxing.

Preparation 4: 2-(10-Methoxy-5,6-dihydropyrido[2',3':4,5]pyrrolo[2,1-a]-isoquinolin-12-yl)ethylamine Step A: 1-{[2-(2-Bromophenyl)-1,3-dioxolan-2-yl]methyl}-5-methoxy-1H-pyrrolo[3,2-b]pyridine Under argon and in an anhydrous medium, 295 mg (2.6 mmol) of potassium tert-butylate are added to a solution containing 300 mg (2 mmol) of the compound obtained in Step B of Preparation 1 and 785 mg (2.4 mmol) of 2-(bromoethyl)-2-(2-bromophenyl)-1,3-dioxolane in 5 ml of dimethyl sulphoxide. The reaction mixture is heated at 100° C. for 24 hours. After returning to room temperature, the mixture is hydrolysed with water and then extracted with ethyl acetate. After washing several times with water, the organic phase is dried over magnesium sulphate, filtered and then evaporated. Purification by flash chromatography over silica gel (eluant:petroleum ether/ethyl acetate, 85:15) yields the title compound in the form of a white solid.

Melting point 143-144° C.

Step B: 1-(2-Bromophenyl)-2-(5-methoxy-1H-pyrrolo[3,2-b]pyridin-1-yl)-1-ethanone A solution containing 1.60 g (4.1 mmol) of the compound obtained in Step A in 10 ml of methanol and 20 ml of 18% hydrochloric acid is refluxed for 4 hours. After returning to room temperature and removal of the methanol by evaporation, the mixture is neutralised with a saturated sodium hydrogen carbonate solution and then extracted with ethyl acetate. The organic phase is dried over magnesium sulphate, filtered and concentrated. The residue is purified by flash chromatography over silica gel (eluant:petroleum ether/ethyl acetate, 8:2) to yield the title compound in the form of a white solid.

Melting point 116-117° C.

Step C: 1-(2-Bromophenethyl)-5-methoxy-1H-pyrrolo[3,2-b]pyridine

140 μl (2.9 mmol) of hydrazine hydrate and 80 mg (2 mmol) of sodium hydroxide are added to a solution of 200 mg (0.6 mmol) of the compound obtained in Step B in 2 ml of diethylene glycol. After 24 hours' stirring at 160° C., the mixture is hydrolysed and then extracted with ethyl acetate. The organic phase is washed several times with water, dried over magnesium sulphate, concentrated and then purified by flash chromatography over silica gel (eluant:petroleum ether/ethyl acetate, 7:3) to yield the title compound in the form of a yellow oil.

Step D: 10-Methoxy-5,6-dihydropyrido[2',3':4,5]pyrrolo[2,1-a]isoquinoline

The title compound is obtained starting from the compound obtained in Step C according to the experimental protocol described in Step D of Preparation 1. Yellow solid.

Melting point: 179-180° C.

Step E: 10-Methoxy-5,6-dihydropyrido[2',3':4,5]pyrrolo[2,1-a]isoquinoline-12-carbaldehyde The same procedure is used as in Step E of Preparation 1. Yellow solid.

Melting point: 192-193° C.

Step F: 2-(10-Methoxy-5,6-dihydropyrido[2',3':4,5]pyrrolo[2,1-a]-isoquinolin-12-yl)ethylamine The procedure is as for Steps F, G and H of Preparation 1. Brown oil.

Melting point (oxalate): 137-138° C.

Preparation 5: 2-(11-Methoxy-6,7-dihydro-5H-pyrido[2',3':4,5]pyrrolo[2,1-a]-[2]-benzazepin-13-yl)ethylamine Step A: 1-[3-(2-Bromophenyl)propyl]-5-methoxy-1H-pyrrolo[3,2-b]pyridine Under argon and in an anhydrous medium, 162 mg (4.05 mmol) of sodium hydride (60% in oil) are added slowly, at 0° C., to a solution of 500 mg (3.38 mmol) of the compound obtained in Step B of Preparation 1 in 10 ml of N,N-dimethylformamide. After 35 minutes' stirring at room temperature, a solution of 1.3 g (4.05 mmol) of 1-bromo-2-(3-iodopropyl)-benzene dissolved in 5 ml of N,N-dimethylformamide is added to the mixture. After 1 hour's stirring at room temperature, the mixture is hydrolysed and then extracted with ethyl acetate. The organic phase is washed several times with water, dried over magnesium sulphate, concentrated and purified by flash chromatography over silica gel (eluant:petroleum ether/ethyl acetate, 8:2) to yield the title compound in the form of a yellow oil.

Step B: 11-Methoxy-6,7-dihydro-5H-pyrido[2',3':4,5]pyrrolo[2,1-a][2]-benzazepine Under an inert atmosphere, 500 mg (1.45 mmol) of the compound obtained in Step A, 81 mg (72.5 μmol) of tetrakis(triphenylphosphine)palladium(0) and 142 mg (1.45 mmol) of potassium acetate in 15 ml of N,N-dimethylacetamide are heated at 160° C. for 2 hours. After returning to room temperature, the reaction mixture is filtered using a Büchner funnel and then evaporated to dryness. The residue is then hydrolysed and subsequently extracted with ethyl acetate. The organic phase is dried over magnesium sulphate, concentrated and purified by flash chromatography over silica gel (eluant:petroleum ether/ethyl acetate, 9:1) to yield the title compound in the form of a colourless oil.

Step C: 11-Methoxy-6,7-dihydro-5H-pyrido[2',3':4,5]pyrrolo[2,1-a][2]-benzazepine-13-carbaldehyde The procedure is as for Step F of Preparation 1.

Step D: 2-(11-Methoxy-6,7-dihydro-5H-pyrido[2',3':4,5]pyrrolo[2,1-a][2]-benzazepin-13-yl)ethylamine The procedure is as for Steps G and H of Preparation 1. Green solid.

Melting point: 114-115° C.

Preparation 6: 4-(6,7-Dihydro-5H-pyrido[2',3':4,5]pyrrolo[2,1-a][2]-benzazepin-13-yl)butanoic acid The procedure is as for Preparation 3 starting from 6,7-dihydro-5H-pyrido[2',3':4,5]pyrrolo[2,1-a][2]benzazepine-13-carbaldehyde (obtained according to a process analogous to Steps A, B and C of Preparation 5).

Preparation 7: 2-(11-Ethyl-6,7-dihydro-5H-pyrido[2',3':4,5]pyrrolo[2,1-a][2]-benzazepin-13-yl)ethylamine The procedure is as for Preparation 5 starting from 2-ethyl-5-nitropyridine.

Preparation 8: 2-(2-Methoxy-6,7,8,9-tetrahydropyrido[2,3-b]indolizin-10-yl)ethylamine Step A: 1-(4-Bromobutyl)-5-methoxy-1H-pyrrolo[3,2-b]pyridine Under argon and in an anhydrous medium, 810 mg (20.27 mmol) of sodium hydride (60% in oil) are added slowly to a solution of 2 g (13.51 mmol) of the compound obtained in Step B of Preparation 1 in 30 ml of N,N-dimethylformamide at 0° C. After stirring for one hour at room temperature, the solution containing the previously formed anion is added dropwise to 4.8 ml (40.54 mmol) of 1,4-dibromobutane. After stirring for two hours at room temperature, the reaction mixture is hydrolysed and then extracted with ethyl acetate. The organic phase is dried over magnesium sulphate, concentrated and purified by flash chromatography over silica gel (eluant:petroleum ether/ethyl acetate, 8:2) to yield the title compound in the form of a colourless oil.

Step B: 1-(4-Bromobutyl)-5-methoxy-1H-pyrrolo[3,2-b]pyridine-3-carbaldehyde

Under argon and in an anhydrous medium, 730 μl (7.95 mmol) of phosphorus oxychloride are added dropwise to 12.5 ml of N,N-dimethylformamide maintained at 0° C.: after 30 minutes' stirring, 1.50 g (5.3 mmol) of the compound obtained in Step A dissolved in 25 ml of N,N-dimethylformamide are added by transfer. The reaction mixture is stirred for 30 minutes at 0° C. and then for 3 hours at room temperature. The reaction mixture is evaporated to dryness and then taken up in water, the aqueous phase is rendered alkaline with a 6N sodium hydroxide solution and extracted several times with ethyl acetate. The combined organic phases are dried over magnesium sulphate, filtered and then evaporated. After washing with a petroleum ether/diethyl ether mixture, the title compound is obtained in the form of a yellow oil.

Step C: 2-Methoxy-6,7,8,9-tetrahydropyrido[2,3-b]indolizine-10-carbaldehyde

Under argon, a solution containing 2.70 g (8.67 mmol) of the compound obtained in Step B and 1.45 g (8.67 mmol) of AIBN in 80 ml of toluene is brought to reflux. After stirring for 20 minutes 4.67 ml (17.35 mmol) of tributyltin hydride in 100 ml of toluene are added to the reaction mixture, which is maintained at reflux for 24 hours. After returning to room temperature and evaporation to dryness, the residue is then hydrolysed and subsequently extracted with ethyl acetate. The organic phase is dried over magnesium sulphate, concentrated and purified by flash chromatography over silica gel (eluant:petroleum ether/ethyl acetate, 95:5) to yield the title product in the form of a yellow oil.

Step D: 2-Methoxy-10-[2-nitroethenyl]-6,7,8,9-tetrahydropyrido[2,3-b]indolizine 550 mg (2.39 mmol) of the compound obtained in Step C dissolved in 25 ml of nitromethane are heated at 120° C. for 3 hours in the presence of 460 mg (5.97 mmol) of ammonium acetate. After returning to room temperature and evaporation to dryness, the reaction mixture is diluted in dichloromethane and washed with water. The organic phase is dried over magnesium sulphate, filtered and evaporated. After washing with a pentane/diethyl ether mixture, the title compound is obtained in the form of a brown solid.

Melting point: 202-203° C.

Step E: 2-Methoxy-10-(2-nitroethyl)-6,7,8,9-tetrahydropyrido[2,3-b]indolizine Under argon and in an anhydrous medium, 650 mg (2.38 mmol) of the compound obtained in Step D are suspended in 10 ml of isopropanol and 30 ml of chloroform in the presence of 1.5 g of 230-400 mesh silica; 450 mg (11.90 mmol) of sodium borohydride are added slowly. After stirring for 30 minutes at room temperature, acetic acid is added and the reaction mixture is filtered over a glass frit. After removal of the solvents by evaporation, the residue is diluted in dichloromethane and washed with water. The organic phase is then dried over magnesium sulphate, filtered and concentrated to yield the title compound in the form of a yellow solid.

Melting point: 96-97° C.

Step F: 2-(2-Methoxy-6,7,8,9-tetrahydropyrido[2,3-b]indolizin-10-yl)ethylamine Under a hydrogen pressure of 55 psi, 420 mg (1.53 mmol) of the compound obtained in Step E and 170 mg of Raney nickel are stirred in 20 ml of methanol at 60° C. for 15 hours. After returning to room temperature, the reaction mixture is filtered using a Büchner funnel and then evaporated to yield the title product in the form of a brown oil.

Preparation 9: 2-(3-Methoxy-6,7,8,9-tetrahydropyrido[3,2-b]indolizin-5-yl)ethylamine

Step A: 3,3,5-Tribromo-1,3-dihydro-2H-pyrrolo[2,3-b]pyridin-2-one

At room temperature, 54 ml (1.05 mol) of bromine are added dropwise to 10 g (84 mmol) of 7-azaindole dissolved in 660 ml of tert-butanol and 660 ml of water. After 19 hours' stirring at room temperature, the tert-butanol is removed by evaporation and the residual aqueous phase is rendered alkaline with an aqueous saturated sodium hydrogen carbonate solution. The desired product is recovered by filtration. After drying in vacuo in the presence of phosphorus pentoxide, the title compound is obtained in the form of a brown oil.

Melting point: 157-158° C.

Step B: 5-Bromo-1,3-dihydro-2H-pyrrolo[2,3-b]pyridin-2-one

Under argon at room temperature, 17.60 g (0.27 mol) of powdered zinc are added in portions to 5 g (13.5 mmol) of the compound obtained in Step A dissolved in 100 ml of acetic acid. After 15 hours' stirring at room temperature, the acetic acid is removed by evaporation under reduced pressure (coevaporation with toluene). The residue, which is taken up in ethyl acetate, is washed once with water: the aqueous phase is washed several times with ethyl acetate. The organic phases are combined, dried over magnesium sulphate, concentrated and purified by flash chromatography over silica gel (eluant:dichloromethane/methanol, 95/5), to obtain the title compound in the form of an orange solid.

Melting point: 250-251° C.

Step C: 5-Bromo-1H-pyrrolo[2,3-b]pyridine

Under an argon atmosphere and in an anhydrous medium, 37.6 ml (37.6 mmol) of a 1M solution of borane-tetrahydrofuran complex in tetrahydrofuran are added at 0° C. and dropwise to a suspension of 2 g (9.4 mmol) of the compound obtained in Step B in 50 ml of anhydrous tetrahydrofuran. The reaction mixture is stirred for 35 minutes at room temperature and then evaporated to dryness. The residue is taken up in an aqueous 6M hydrochloric acid solution and heated until the solid has completely dissolved. After cooling, the solution is rendered alkaline with an aqueous 6M sodium hydroxide solution and extracted with ethyl acetate. After drying over magnesium sulphate and evaporation, an equimolar mixture of 5-bromo-7-azaindoline and 5-bromo-7-azaindole is obtained. The preceding residue, which is dissolved in 20 ml of acetic acid, is added at room temperature to a suspension of 4.10 g (15.3 mmol) manganese(III) acetate dihydrate in 20 ml of acetic acid. After 45 minutes' stirring at 75° C. the solution is evaporated to dryness and coevaporated with toluene. The residue, which is taken up in water, is rendered alkaline with an aqueous saturated sodium hydrogen carbonate solution. After extraction with ethyl acetate the organic phases are dried over magnesium sulphate and evaporated. The resulting residue is purified by flash chromatography over silica gel (eluant:petroleum ether/ethyl acetate) to yield the title compound in the form of a yellow solid.

Melting point: 176-177° C.

Step D: 5-Methoxy-1H-pyrrolo[2,3-b]pyridine

Under an argon atmosphere and in an anhydrous medium, 1 g (5.07 mmol) of the compound obtained in Step C is dissolved in a mixture of 25 ml of N,N-dimethylformamide and 22 ml of methanol; 6.86 g (126.75 mmol) of sodium methanolate and 1.43 g (10.30 mmol) of copper(I) bromide are added at room temperature. The mixture is heated at reflux for 3 hours. After removal of the solvents by evaporation, the residue is taken up in water and ethyl acetate and then filtered over Celite. The organic phase is washed with water, dried over magnesium sulphate and evaporated to yield a solid, which is purified by flash chromatography over silica gel (eluant:petroleum ether/ethyl acetate, 7:3). The title compound is obtained in the form of a brown solid.
Melting point: 162-163° C.

Step E: 2-(3-Methoxy-6,7,8,9-tetrahydropyrido[3,2-b]indolizin-5-yl)ethylamine The procedure is as for A, B, C, D, E and F of Preparation 8 starting from the compound obtained in Step D. Brown oil.

Preparation 10: 4-(2-Methoxy-6,7,8,9-tetrahydropyrido[2,3-b]indolizin-10-yl)butanoic acid The procedure is as for Preparation 3 starting from the compound obtained in Step C of Preparation 8.

Preparation 11: 2-(2-Methoxy-7,8-dihydro-6H-pyrido[2,3-b]pyrrolizin-9-yl)-ethylamine The procedure is as for Preparation 8, in Step A replacing 1,4-dibromobutane by 1.4-dibromopropane.

Preparation 12: 2-(2-Isopropyl-7,8-dihydro-6H-pyrido[2,3-b]pyrrolizin-9-yl)-ethylamine The procedure is as for Preparation 8, in Step A replacing 5-methoxy-1H-pyrrolo[3,2-b]-pyridine by 5-isopropyl-1H-pyrrolo[3,2-b]pyridine and 1,4-dibromobutane by 1,3-dibromopropane.

Preparation 13: 2-[2-(Benzyloxy)-7,8,9,10-tetrahydro-6H-pyrido[2',3':4,5]pyrrolo-[1,2-a]azepin-11-yl]ethylamine The procedure is as for Preparation 8, in Step A replacing 5-methoxy-1H-pyrrolo[3,2-b]-pyridine by 5-benzyloxy-1H-pyrrolo[3,2-b]pyridine and 1,4-dibromobutane by 1,5-dibromopentane.

Preparation 14: 2-(8-Methoxy-3,4-dihydro-2H-pyrido[2',3':4,5]pyrrolo[2,1-b][1,3]-oxazin-10-yl)ethylamine

Step A: 1-[3-(Benzyloxy)propyl]-5-methoxy-1H-pyrrolo[3,2-b]pyridine

Under argon and in an anhydrous medium, 973 mg of sodium hydride (60% in oil) (24.32 mmol) are added slowly, at 0° C., to a solution of 3 g (20.27 mmol) of the compound obtained in Step B of Preparation 1 in 90 ml of N,N-dimethylformamide. After 45 minutes' stirring at room temperature, a solution of 4.3 ml (24.32 mmol) of 1-benzyloxy-3-bromopropane dissolved in 10 ml of N,N-dimethylformamide is added to the mixture. After 2 hours' stirring at room temperature, the mixture is hydrolysed and then extracted with ethyl acetate. The organic phase is washed several times with water, dried over magnesium sulphate, concentrated and purified by flash chromatography over silica gel (eluant:petroleum ether/ethyl acetate, 7:3) to yield the title compound in the form of a yellow oil.

Step B: 1-[3-(Benzyloxy)propyl]-3,3-dibromo-5-methoxy-1,3-dihydro-2H-pyrrolo[3,2-b]pyridin-2-one At room temperature, 1.74 ml (33.78 mmol) of bromine are added dropwise to 2 g (6.75 mmol) of the compound obtained in Step A dissolved in 55 ml of tert-butanol and 55 ml of water. After 10 hours' stirring at room temperature, the tert-butanol is removed by evaporation and the residual aqueous phase is rendered alkaline with an aqueous saturated sodium hydrogen carbonate solution and then extracted with dichloromethane. The organic phase is dried over magnesium sulphate, filtered and concentrated. The residue is purified by flash chromatography over silica gel (eluant:petroleum ether/ethyl acetate, 9:1) to yield the title compound in the form of a brown oil.

Step C: 1-[3-(Benzyloxy)propyl]-5-methoxy-1,3-dihydro-2H-pyrrolo[3,2-b]-pyridin-2-one Under argon and at room temperature, 1.10 g (16.8 mmol) of powdered zinc are added in portions to 789 mg (1.68 mmol) of the compound obtained in Step B dissolved in 15 ml of acetic acid. After 5 hours' stirring at room temperature, the reaction mixture is filtered using a Büchner funnel, evaporated to dryness and then coevaporated in the presence of toluene. The residue, which is taken up in ethyl acetate, is washed several times with water. The organic phase is dried over magnesium sulphate, filtered and concentrated and then purified by flash chromatography over silica gel (eluant:petroleum ether/ethyl acetate, 1:1) to yield the title compound in the form of an orange oil.

Step D: 1-(3-Hydroxypropyl)-5-methoxy-1,3-dihydro-2H-pyrrolo[3,2-b]pyridin-2-one Under a hydrogen pressure of 45 psi, 510 mg (1.63 mmol) of the compound obtained in Step C and 72 mg of palladium-on-carbon suspended in 10 ml of methanol are stirred for 15 hours at room temperature. After filtration over Celite and evaporation, the residue is hydrolysed with water and then extracted with ethyl acetate. The organic phase is dried over magnesium sulphate and evaporated to yield the title compound in the form of a brown solid.
Melting point: 121-122° C.

Step E: 1-(3-Bromopropyl)-5-methoxy-1,3-dihydro-2H-pyrrolo[3,2-b]pyridin-2-one Under argon and in an anhydrous medium, 1.50 g (3.76 mmol) of 1.2-bis-diphenylphosphinoethane are added at 0° C. to a solution of 1.25 g (3.76 mmol) of carbon tetrabromide in 20 ml of dichloromethane. After 10 minutes at 0° C., 417 mg (1.88 mmol) of the compound obtained in Step D dissolved in 10 ml of dichloromethane are added to the mixture. The mixture is stirred for 30 minutes at 0° C., and then for 3 hours at room temperature. After hydrolysis of the reaction mixture, the organic phase is dried over magnesium sulphate, filtered and concentrated. Purification by flash chromatography over silica gel (eluant:petroleum ether/ethyl acetate, 8:2) yields the title compound in the form of a white solid.

Melting point: 82-83° C.

Step F: 8-Methoxy-3,4-dihydro-2H-pyrido[2',3':4,5]pyrrolo[2,1-b][1,3]oxazine Under an inert atmosphere, 160 mg (4 mmol) of sodium hydride (60% in oil) are added slowly at 0° C. to a solution of 380 mg (1.34 mmol) of the compound obtained in Step E in 10 ml of N,N-dimethylformamide. The reaction mixture is stirred at 0° C. for 30 minutes before being hydrolysed with ice and then extracted with ethyl acetate. The organic phase is washed several times with water, dried over magnesium sulphate, concentrated and purified by flash chromatography over silica gel (eluant:ethyl acetate/petroleum ether, 95:5) to yield the title compound in the form of a brown solid.

Melting point: 92-93° C.

Step G: 8-Methoxy-3,4-dihydro-2H-pyrido[2',3':4,5]pyrrolo[2,1-b][1,3]oxazine-10-carbaldehyde Under argon and in an anhydrous medium, 216 µl (2.35 mmol) of phosphorus oxychloride are added dropwise to 3.5 ml of N,N-dimethylformamide maintained at 0° C.; after 15 minutes' stirring, 320 mg (1.56 mmol) of the compound obtained in Step G dissolved in 5 ml of N,N-dimethylformamide are added by transfer. The reaction mixture is stirred for 30 minutes at 0° C. and then for 2 hours at room temperature. The reaction mixture is evaporated to dryness and then taken up in water; the aqueous phase is rendered alkaline with a 6N sodium hydroxide solution and extracted several times with ethyl acetate. The combined organic phases are dried over magnesium sulphate and evaporated to yield the title compound in the form of a brown solid.

Melting point: 224-225° C.

Step H: 8-Methoxy-10-[2-nitroethenyl]-3,4-dihydro-2H-pyrido[2',3':4,5]-pyrrolo [2,1-b][1,3]oxazine 300 mg (1.29 mmol) of the compound obtained in Step G dissolved in 15 ml of nitromethane are heated at 120° C. for 4 hours in the presence of 250 mg (3.23 mmol) of ammonium acetate. After returning to room temperature and evaporation to dryness, the reaction mixture is diluted in dichloromethane and washed with water. After drying over magnesium sulphate, evaporation of the organic phase yields the title compound in the form of a yellow solid.

Melting point: 248-249° C.

Step I: 8-Methoxy-10-(2-nitroethyl)-3,4-dihydro-2H-pyrido[2',3':4,5]-pyrrolo[2,1-b][1,3]oxazine Under argon and in an anhydrous medium, 340 mg (1.23 mmol) of the compound obtained in Step H are suspended in 7 ml of isopropanol and 21 ml of chloroform in the presence of 810 mg of 230-400 mesh silica; 234 mg (6.18 mmol) of sodium borohydride are added slowly. After 2 hours' stirring at room temperature, acetic acid is added and the reaction mixture is filtered through a glass frit. After removal of the solvents by evaporation, the residue is diluted in dichloromethane and washed with water. The organic phase is then dried over magnesium sulphate, filtered, concentrated and purified by flash chromatography over silica gel (eluant:ethyl acetate/petroleum ether, 6:4) to yield the title compound in the form of a yellow solid.

Melting point: 104-105° C.

Step J: 2-(8-Methoxy-3,4-dihydro-2H-pyrido[2',3':4,5]pyrrolo[2,1-b][1,3]-oxazin-10-yl)ethylamine Under a hydrogen pressure of 55 psi, 410 mg (1.48 mmol) of the compound obtained in Step I and 165 mg of Raney nickel are stirred in 20 ml of methanol at 60° C. for 15 hours. After returning to room temperature, the reaction mixture is filtered using a Büchner funnel and then evaporated to yield the title amine in the form of a brown oil.

Melting point (oxalate): 84-85° C.

Preparation 15: 2-(8-Methoxy-3,4-dihydro-2H-pyrido[4',3':4,5]pyrrolo[2,1-b][1,3]-oxazin-10-yl)ethylamine The procedure is as for Preparation 14 starting from 5-methoxy-1H-pyrrolo-[2,3-c]pyridine.

Preparation 16: 2-(2-Methoxy-6,7,8,9-tetrahydropyrido[2',3':4,5]pyrrolo[2,1-b]oxazepin-11-yl)ethylamine The procedure is as for Preparation 14, in Step A replacing 1-benzyloxy-3-bromopropane by 1-benzyloxy-4-bromobutane.

Preparation 17: 2-(8-Methoxy-3,4-dihydro-2H-pyrido[3',2':4,5]pyrrolo[2,1-b][1,3]-oxazin-10-yl)ethylamine

Step A: 1-[3-(Benzyloxy)propyl]-5-bromo-1H-pyrrolo[2,3-b]pyridine

The procedure is as for Step A of Preparation 14 starting from the compound obtained in Step C of Preparation 9.

Step B: 1-[3-(Benzyloxy)propyl]-5-methoxy-1H-pyrrolo[2,3-b]pyridine

Under argon and in an anhydrous medium, 6.1 g (17.67 mmol) of the compound obtained in Step A are dissolved in a mixture of 115 ml of N,N-dimethylformamide and 110 ml of methanol; 24 g (0.44 mol) of sodium methanolate and 2.53 g (17.67 mmol) of copper(I) bromide are added at room temperature. The mixture is heated at reflux for 4 hours. After removal of the solvents by evaporation, the residue is taken up in ethyl acetate and filtered over Celite. The filtrate is washed with water. The organic phase is dried over magnesium sulphate, concentrated and purified by flash chromatography over silica gel (eluant:petroleum ether/ethyl acetate, 7:3) to yield the title compound in the form of a yellow oil.

Step C: 2-(8-Methoxy-3,4-dihydro-2H-pyrido[3',2':4,5]pyrrolo[2,1-b][1,3]-oxazin-10-yl)ethylamine The procedure is as for Steps B, C, D, E, F, G, H, I and J of Preparation 14 starting from the compound obtained in Step B. Brown oil.

Preparation 18: 11-(2-Aminoethyl)-2-methoxy-6H-pyrido[2',3':4,5]pyrrolo[2,1-a]isoindol-6-one Step A: 5-Methoxy-1H-pyrrolo[3,2-b]pyridine-3-carbaldehyde The procedure is as for Step E of Preparation 1 from the compound obtained in Step B of Preparation 1.

Step B: 1-(2-Iodobenzoyl)-5-methoxy-1H-pyrrolo[3,2-b]pyridine-3-carbaldehyde

Under an argon atmosphere, 0.56 mmol of the compound obtained in Step A are dissolved in 5 ml of DMF, and then 0.68 mmol of NaH are added at 0° C. over a period of 30 minutes. After 30 minutes' stirring at 0° C., 0.68 mmol of 2-iodobenzoyl chloride dissolved in 5 ml of DMF is added dropwise to the mixture. After 3 hours' stirring, the solvents are removed by evaporation and the residue is taken up in water and extracted with dichloromethane. After drying over magnesium sulphate and removal of the solvents by evaporation, the residue is purified by flash chromatography over silica gel (eluant:petroleum ether/ethyl acetate) to yield the title compound.

Step C: 2-Methoxy-6-oxo-6H-pyrido[2',3':4,5]pyrrolo[2,1-a]isoindole-11-carbaldehyde Under an argon atmosphere, 0.49 mmol of the compound obtained in Step B, 0.2 mmol of tetrakis(triphenylphosphine)palladium(0) and 0.49 mmol of potassium acetate in 15 ml of DMF are heated at 140° C. for 3 hours. After returning to room temperature, the reaction mixture is filtered using a Büchner funnel and then evaporated to dryness. The residue is then hydrolysed and subsequently extracted with ethyl acetate. The organic phase is dried over magnesium sulphate and concentrated, and the residue is purified by flash chromatography over silica gel (eluant:petroleum ether/ethyl acetate) to yield the title compound.

Step D: 11-(2-Aminoethyl)-2-methoxy-6H-pyrido[2',3':4,5]pyrrolo[2,1-a]isoindol-6-one The procedure is as for Steps F-H of Preparation 1.

EXAMPLE 1

N-[2-(2-Methoxy-6H-pyrido[2',3':4,5]pyrrolo[2,1-a]isoindol-11-yl)-ethyl]acetamide Under argon and in an anhydrous medium, 470 mg (1.68 mmol) of the compound obtained in Preparation 1 are dissolved in 15 ml of dichloromethane and 350 µl of pyridine; at 0° C., 175 µl (1.85 mmol) of acetic anhydride are added. The reaction mixture is stirred for 3 hours at room temperature before being hydrolysed with water. The aqueous phase is neutralised with a saturated sodium hydrogen carbonate solution and extracted with dichloromethane. After drying over magnesium sulphate and removal of the solvents by evaporation, the residue is purified by flash chromatography over silica gel (eluant:ethyl acetate/petroleum ether, 8:2); after washing with a pentane/diethyl ether mixture, the title compound is obtained in the form of a white solid.

Melting point: 96-97° C. Elemental microanalysis:

| % | C | H | N |
|---|---|---|---|
| Calculated: | 71.01 | 5.96 | 13.07 |
| Found: | 70.59 | 5.74 | 12.59 |

EXAMPLE 2

N-[2-(2-Methoxy-6H-pyrido[2',3':4,5]pyrrolo[2,1-a]isoindol-11-yl)-ethyl]-2-furamide The procedure is as for Example 1, replacing acetic anhydride by 2-furoyl chloride. White solid.

Melting point: 143-144° C. Elemental microanalysis:

| % | C | H | N |
|---|---|---|---|
| Calculated: | 70.76 | 5.13 | 11.25 |
| Found: | 70.54 | 5.10 | 10.80 |

EXAMPLE 3

N-[2-(2-Methoxy-6H-pyrido[2',3':4,5]pyrrolo[2,1-a]isoindol-11-yl)-ethyl]benzamide The procedure is as for Example 1, replacing acetic anhydride by benzoyl chloride.

Melting point: 177-178° C. Elemental microanalysis:

| % | C | H | N |
|---|---|---|---|
| Calculated: | 75.18 | 5.52 | 10.96 |
| Found: | 74.81 | 5.41 | 10.67 |

EXAMPLE 4

N-[2-(2-Methoxy-6H-pyrido[2',3':4,5]pyrrolo[2,1-a]isoindol-11-yl)-ethyl]cyclopropanecarboxamide The procedure is as for Example 1, replacing acetic anhydride by cyclopropanecarbonyl chloride.

EXAMPLE 5

N-[2-(2-Methoxy-6H-pyrido[2',3':4,5]pyrrolo[2,1-a]isoindol-11-yl)-ethyl]-N'-methylurea The procedure is as for Example 1, replacing acetic anhydride by methyl isocyanate.

EXAMPLE 6

N-{2-[2-Methoxy-8-(trifluoromethyl)-6H-pyrido[2',3':4,5]pyrrolo[2,1-a]-isoindol-11-yl]ethyl}acetamide The procedure is as for Example 1 starting from the compound obtained in Preparation 2.

EXAMPLE 7

4-(2-Methoxy-6H-pyrido[2',3':4,5]pyrrolo[2,1-a]isoindol-11-yl)-N-methylbutanamide The title product is obtained by condensation of N-methylamine with the compound obtained in Preparation 3 after conversion to the corresponding acid chloride.

EXAMPLE 8

N-[2-(10-Methoxy-5,6-dihydropyrido[2',3':4,5]pyrrolo[2,1-a]-isoquinolin-12-yl)ethyl]-2-furamide The procedure is as for Example 2 starting from the compound obtained in Preparation 4.

Melting point: 188-189° C. Elemental microanalysis:

| % | C | H | N |
|---|---|---|---|
| Calculated: | 71.30 | 5.46 | 10.85 |
| Found: | 70.65 | 5.44 | 10.63 |

EXAMPLE 9

N-[2-(10-Methoxy-5,6-dihydropyrido[2',3':4,5]pyrrolo[2,1-a]-isoquinolin-12-yl)ethyl]-2-phenylacetamide The procedure is as for Example 8, replacing 2-furoyl chloride by benzoyl chloride.

EXAMPLE 10

N-[2-(11-Methoxy-6,7-dihydro-5H-pyrido[2',3':4,5]pyrrolo[2,1-a][2]-benzazepin-13-yl)ethyl]acetamide Under argon and in an anhydrous medium, 550 mg (1.79 mmol) of the compound obtained in Preparation 5 are dissolved in 15 ml of dichloromethane and 372 µl of pyridine; at 0° C., 186 µl (1.97 mmol) of acetic anhydride are added. The reaction mixture is stirred for 5 hours at room temperature before being hydrolysed with water. The aqueous phase is neutralised with a saturated sodium hydrogen carbonate solution and extracted with dichloromethane. After drying over magnesium sulphate and removal of the solvents by evaporation, the residue is purified by flash chromatography over silica gel (eluant:dichloromethane/methanol, 99:1); after washing with a pentane/diethyl ether mixture, the title compound is obtained in the form of a white solid.

Melting point: 73-74° C. Elemental microanalysis:

| % | C | H | N |
|---|---|---|---|
| Calculated: | 72.12 | 6.63 | 12.03 |
| Found: | 71.99 | 6.67 | 11.56 |

EXAMPLE 11

N-[2-(11-Methoxy-6,7-dihydro-5H-pyrido[2',3':4,5]pyrrolo[2,1-a][2]-benzazepin-13-yl)ethyl]-2-furamide Under argon and in an anhydrous medium, 730 mg (2.38 mmol) of the compound obtained in Preparation 5 are dissolved in 10 ml of dichloromethane and 1 ml (7.13 mmol) of triethylamine; at 0° C., 330 µl (3.33 mmol) of 2-furoyl chloride are added. The reaction mixture is stirred for 15 hours at room temperature before being hydrolysed with water and subsequently extracted with dichloromethane. After drying over magnesium sulphate and removal of the solvents by evaporation, the residue is purified by flash chromatography over silica gel (eluant:petroleum ether/ethyl acetate, 6:4) and then by washing with a hexane/petroleum ether mixture to yield the title compound in the form of a white solid.

Melting point: 70-71° C. Elemental microanalysis:

| % | C | H | N |
|---|---|---|---|
| Calculated: | 71.80 | 5.88 | 10.21 |
| Found: | 71.39 | 5.77 | 10.47 |

EXAMPLE 12

N-[2-(11-Hydroxy-6,7-dihydro-5H-pyrido[2',3':4,5]pyrrolo[2,1-a][2]-benzazepin-13-yl)ethyl]-2-furamide Under an inert atmosphere, 582 mg (4.36 mmol) of aluminium chloride are added to a solution of 350 mg (0.87 mmol) of the compound of Example 11 in 15 ml of dichloromethane. The reaction mixture is refluxed for 6 hours before being hydrolysed with water. The aqueous phase is neutralised with a sodium hydrogen carbonate solution and extracted with dichloromethane. After drying over magnesium sulphate and removal of the solvents by evaporation, the residue is purified by flash chromatography over silica gel (eluant:ethyl acetate/methanol, 95:5) and then by washing with a hexane/diethyl ether mixture to yield the title compound in the form of a white solid.

Melting point: >260° C.

EXAMPLE 13

N-Cyclobutyl-4-(6,7-dihydro-5H-pyrido[2',3':4,5]pyrrolo[2,1-a][2]-benzazepin-13-yl)butanamide The procedure is as for Example 7 from the compound obtained in Preparation 6 and replacing N-methylamine by N-cyclobutylamine.

EXAMPLE 14

N-[2-(11-Ethyl-6,7-dihydro-5H-pyrido[2',3':4,5]pyrrolo[2,1-a]-benzazepin-13-yl)ethyl]acetamide The procedure is as for Example 10 starting from the compound obtained in Preparation 7.

EXAMPLE 15

N-[2-(2-Methoxy-6,7,8,9-tetrahydropyrido[2,3-b]
indolizin-10-yl)ethyl]-acetamide Under argon and in an anhydrous medium, 367 mg (1.49 mmol) of the compound obtained in Preparation 8 are dissolved in 15 ml of dichloromethane and 320 µl of pyridine; at 0° C., 160 µl (1.64 mmol) of acetic anhydride are added. The reaction mixture is stirred for 3 hours at room temperature before being hydrolysed with water. The aqueous phase is neutralised with a saturated sodium hydrogen carbonate solution and extracted with dichloromethane. After drying over magnesium sulphate and removal of the solvents by evaporation, the residue is purified by flash chromatography over silica gel (eluant:ethyl acetate); after washing with a pentane/diethyl ether mixture, the title compound is obtained in the form of a white solid.

Melting point: 89-90° C. Elemental microanalysis:

| % | C | H | N |
|---|---|---|---|
| Calculated: | 66.88 | 7.37 | 14.62 |
| Found: | 66.12 | 7.10 | 14.57 |

EXAMPLE 16

N-[2-(2-Methoxy-6,7,8,9-tetrahydropyrido[2,3-b]
indolizin-10-yl)ethyl]-2-furamide Under argon and in an anhydrous medium, 310 mg (1.27 mmol) of the compound obtained in Preparation 8 are dissolved in 15 ml of dichloromethane and 530 µl (3.79 mmol) of triethylamine; at 0° C., 176 µl (1.77 mmol) of 2-furoyl chloride are added. The reaction mixture is stirred for 3 hours at room temperature before being hydrolysed with water and then extracted with dichloromethane. After drying over magnesium sulphate and removal of the solvents by evaporation, the residue is purified by flash chromatography over silica gel (eluant:petroleum ether/ethyl acetate, 1:1) and then by washing with a hexane/petroleum ether mixture to yield the title compound in the form of a white solid.

Melting point: 104-105° C. Elemental microanalysis:

| % | C | H | N |
|---|---|---|---|
| Calculated: | 70.76 | 5.13 | 11.25 |
| Found: | 70.54 | 5.10 | 10.80 |

EXAMPLE 17

N-[2-(3-Methoxy-6,7,8,9-tetrahydropyrido[2,3-b]
indolizin-5-yl)ethyl]-acetamide

Under argon and in an anhydrous medium, 262 mg (1.07 mmol) of the compound obtained in Preparation 9 are dissolved in 10 ml of dichloromethane and 220 µl of pyridine; at 0° C., 110 µl (1.18 mmol) of acetic anhydride are added. The reaction mixture is stirred for 3 hours at room temperature before being hydrolysed with water. The aqueous phase is neutralised with a saturated sodium hydrogen carbonate solution and extracted with dichloromethane. After drying over magnesium sulphate and removal of the solvents by evaporation, the residue is purified by flash chromatography over silica gel (eluant:ethyl acetate); after washing with a pentane/diethyl ether mixture, the title compound is obtained in the form of a white solid.

Melting point: 148-149° C. Elemental microanalysis:

| % | C | H | N |
|---|---|---|---|
| Calculated: | 66.88 | 7.37 | 14.62 |
| Found: | 66.70 | 7.37 | 14.18 |

EXAMPLE 18

N-[2-(2-Methoxy-6,7,8,9-tetrahydropyrido[2,3-b]
indolizin-10-yl)ethyl]-N'-phenylurea The procedure is as for Example 5 starting from the compound obtained in Preparation 8, replacing methyl isocyanate by phenyl isocyanate.

EXAMPLE 19

N-Cyclopropyl-4-(2-methoxy-6,7,8,9-tetrahydropyrido[2,3-b]indolizin-10-yl)butanamide The procedure is as for Example 7 from the compound obtained in Preparation 10 and replacing N-methylamine by N-cyclopropylamine.

EXAMPLE 20

N-[2-(2-Methoxy-7,8-dihydro-6H-pyrido[2,3-b]pyrrolizin-9-yl)ethyl]-acetamide

The procedure is as for Example 15 starting from the compound obtained in Preparation 11.

EXAMPLE 21

N-[2-(2-Isopropyl-7,8-dihydro-6H-pyrido[2,3-b]
pyrrolizin-9-yl)ethyl]-acetamide

The procedure is as for Example 15 starting from the compound obtained in Preparation 12.

EXAMPLE 22

N-{2-[2-(Benzyloxy)-7,8,9,10-tetrahydro-6H-pyrido
[2',3':4,5]pyrrolo-[1,2-a]azepin-11-yl]
ethyl}heptanamide The procedure is as for Example 1 starting from the compound obtained in Preparation 13, replacing acetic anhydride by heptanoyl chloride.

EXAMPLE 23

N-[2-(8-Methoxy-3,4-dihydro-2H-pyrido[2',3':4,5]
pyrrolo[2,1-b][1,3]-oxazin-10-yl)ethyl]acetamide Under argon and in an anhydrous medium, 350 mg (1.41 mmol) of the compound obtained in Preparation 14 are dissolved in 12 ml of dichloromethane and 300 µl of pyridine; at 0° C., 150 μl (1.56 mmol) of acetic anhydride are added. The reaction mixture is stirred for 6 hours at room temperature before being hydrolysed with water. The aqueous phase is neutralised with a saturated sodium hydrogen carbonate solution and extracted with dichloromethane. After drying over magnesium sulphate and removal of the solvents by evaporation, the residue is purified by flash chromatography over silica gel (eluant:ethyl acetate); after washing with a pentane/diethyl ether mixture, the title compound is obtained in the form of a white solid.

Melting point: 92-93° C. Elemental microanalysis:

| % | C | H | N |
|---|---|---|---|
| Calculated: | 62.27 | 6.62 | 14.52 |
| Found: | 62.02 | 6.66 | 14.40 |

EXAMPLE 24

N-[2-(8-Methoxy-3,4-dihydro-2H-pyrido[2',3':4,5] pyrrolo[2,1-b][1,3]-oxazin-10-yl)ethyl]-2-furamide Under argon and in an anhydrous medium, 200 mg (0.81 mmol) of the compound obtained in Preparation 14 are dissolved in 6 ml of dichloromethane and 340 μl (2.43 mmol) of triethylamine; at 0° C., 115 μl (1.13 mmol) of 2-furoyl chloride are added. The reaction mixture is stirred for 15 hours at room temperature before being hydrolysed with water and then extracted with dichloromethane. After drying over magnesium sulphate and removal of the solvents by evaporation, the residue is purified by flash chromatography over silica gel (eluant:petroleum ether/ethyl acetate, 1:1) and then by washing with a hexane/petroleum ether mixture to yield the title compound in the form of a white solid.

Melting point: 139-140° C. Elemental microanalysis:

| % | C | H | N |
|---|---|---|---|
| Calculated: | 63.33 | 5.61 | 12.31 |
| Found: | 63.52 | 5.64 | 11.93 |

EXAMPLE 25

N-[2-(8-Methoxy-3,4-dihydro-2H-pyrido[4',3':4,5] pyrrolo[2,1-b][1,3]-oxazin-10-yl)ethyl/pentanamide The procedure is as for Example 23 starting from the compound obtained in Preparation 15, replacing acetic anhydride by pentanoyl chloride.

EXAMPLE 26

N-[2-(2-Methoxy-6,7,8,9-tetrahydropyrido[2',3':4,5] pyrrolo[2,1-b][1,3]-oxazepin-11-yl)ethyl]acetamide The procedure is as for Example 23 starting from the compound obtained in Preparation 16.

EXAMPLE 27

N-[2-(8-Methoxy-3,4-dihydro-2H-pyrido[3',2':4,5] pyrrolo[2,1-b][1,3]-oxazin-10-yl)ethyl]-2-furamide Under argon and in an anhydrous medium, 218 mg (0.88 mmol) of the compound obtained in Preparation 17 are dissolved in 10 ml of dichloromethane and 370 μl (2.64 mmol) of triethylamine; at 0° C., 122 μl (1.23 mmol) of 2-furoyl chloride are added. The reaction mixture is stirred for 3 hours at room temperature before being hydrolysed with water and then extracted with dichloromethane. After drying over magnesium sulphate and removal of the solvents by evaporation, the residue is purified by flash chromatography over silica gel (eluant:petroleum ether/ethyl acetate, 1:1) and then by washing with a hexane/petroleum ether mixture to yield the title compound in the form of a white solid.

Melting point: 70-71° C.

EXAMPLE 28

2-Iodo-N-[2-(2-methoxy-6H-pyrido[2',3':4,5]pyrrolo [2,1-a]isoindol-11-yl)ethyl]benzamide Under an argon atmosphere, 1.14 mmol of the compound obtained in Preparation 1 are dissolved in 10 ml of dichloromethane and 3.43 mmol of triethylamine. At 0° C., 1.60 mmol of 2-iodobenzoyl chloride dissolved in 5 ml of dichloromethane are added dropwise to the mixture. The reaction mixture is stirred for 18 hours at room temperature before being hydrolysed with water, and then extracted with dichloromethane. After drying over magnesium sulphate and removal of the solvents by evaporation, the residue is purified by flash chromatography over silica gel (eluant: petroleum ether/ethyl acetate, 1/1) to yield the title compound in the form of a white solid.

Melting point: 224-225° C.

EXAMPLE 29

N-[2-(2-Methoxy-6-oxo-6H-pyrido[2',3':4,5]pyrrolo [2,1-a]isoindol-11-yl)ethyl]-2-furamide Under an argon atmosphere, 1 mmol of the compound obtained in Preparation 18 is dissolved in 10 ml of dichloromethane and 3 mmol of triethylamine, and then 1.4 mmol of 2-furoyl chloride are added dropwise at 0° C. The reaction mixture is stirred for 18 hours before being hydrolysed with water, and then extracted with dichloromethane. After drying over magnesium sulphate and removal of the solvents by evaporation, the residue is purified by flash chromatography over silica gel (eluant:petroleum ether/ethyl acetate) to yield the title compound.

EXAMPLE 30

N-[2-(2-Hydroxy-6,7,8,9-tetrahydropyrido[2,3-b] indolizin-10-yl)ethyl]-2-furamide Under argon and in an anhydrous medium, 0.884 mmol of the compound obtained in Example 16 is dissolved in 16 ml of dichloromethane, and then 4.42 mmol of aluminium chloride are added. The reaction mixture is stirred at reflux for 18 hours. The reaction mixture is hydrolysed, and then neutralised with a sodium hydrogen carbonate solution. After extraction with dichloromethane, the organic phases are dried over magnesium sulphate and evaporated in vacuo. The resulting residue is washed with hexane and diethyl ether to yield the title product.

Melting point: 270° C. Elemental microanalysis:

| % | C | H | N |
|---|---|---|---|
| Calculated: | 66.45 | 5.89 | 12.91 |
| Found: | 65.02 | 6.04 | 12.54 |

Pharmacological Study

EXAMPLE A

Acute Toxicity Study

Acute toxicity was evaluated after oral administration to groups each comprising 8 mice (26±2 grams). The animals were observed at regular intervals during the course of the first day, and daily for the two weeks following treatment. The $LD_{50}$ (the dose that causes the death of 50% of the animals) was evaluated and demonstrated the low toxicity of the compounds of the invention.

EXAMPLE B

Melatonin Receptor Binding Study on Pars Tuberalis Cells of Sheep

Melatonin receptor binding studies of the compounds of the invention were carried out according to conventional techniques on pars tuberalis cells of sheep. The pars tuberalis of the adenohypophysis is in fact characterised in mammals by a high density of melatonin receptors (Journal of Neuroendocrinology, 1, pp. 14, 1989).

Protocol
1) Sheep pars tuberalis membranes are prepared and used as target tissue in saturation experiments to determine the binding capacities and affinities for 2-[$^{125}$I]-iodomelatonin.
2) Sheep pars tuberalis membranes are used as target tissue in competitive binding experiments using the various test compounds in comparison with melatonin.

Each experiment is carried out in triplicate and a range of different concentrations is tested for each compound. The results, after statistical processing, enable the binding affinities of the compound tested to be determined.

Results

The compounds of the invention appear to have a strong affinity for melatonin receptors.

EXAMPLE C

1. Melatonin $mt_1$ and $MT_2$ Receptor Binding Study

The $mt_1$ or $MT_2$ receptor binding experiments are carried out using 2-[$^{125}$I]-iodomelatonin as reference radioligand. The radioactivity retained is determined using a liquid scintillation counter.

Competitive binding experiments are then carried out in triplicate using the various test compounds. A range of different concentrations is tested for each compound. The results enable the binding affinities of the compounds tested ($IC_{50}$) to be determined.

2. Study of Binding at Melatonin $MT_3$ Binding Sites

The studies of binding at $MT_3$ sites are carried out on hamster brain membranes using 2-[$^{125}$I] iodomelatonin as radioligand. The membranes are incubated for 30 minutes with 2-[$^{125}$I] iodomelatonin at a temperature of 4° C. and different concentrations of the test compounds. After incubation, the membranes are rapidly filtered and then washed with cold buffer using a filtration system. The radioactivity fixed is measured using a scintillation counter. The $IC_{50}$ values (concentration that inhibits specific binding by 50%) are calculated from competition curves according to a non-linear regression model.

Thus, the $IC_{50}$ values found for the compounds of the invention demonstrate binding to one or other of the receptor sub-types, those values being $\leq 10$ μM.

EXAMPLE D

Action of the Compounds of the Invention on the Circadian Rhythms of Locomotive Activity of the Rat The involvement of melatonin in influencing the majority of physiological, biochemical and behavioural circadian rhythms by day/night alternation has made it possible to establish a pharmacological model for research into melatoninergic ligands.

The effects of the compounds are tested in relation to numerous parameters and, in particular, in relation to the circadian rhythms of locomotive activity, which are a reliable indicator of the activity of the endogenous circadian clock.

In this study, the effects of such compounds on a particular experimental model, namely the rat placed in temporal isolation (permanent darkness) are evaluated.

Experimental Protocol

One-month-old male rats are subjected, as soon as they arrive at the laboratory, to a light cycle of 12 hours of light per 24 hours (LD 12:12). After 2 to 3 weeks' adaptation, they are placed in cages fitted with a wheel connected to a recording system in order to detect the phases of locomotive activity and thus monitor the nyctohemeral (LD) or circadian (DD) rhythms.

As soon as the rhythms recorded show a stable pattern in the light cycle LD 12:12, the rats are placed in permanent darkness (DD).

Two to three weeks later, when the free course (rhythm reflecting that of the endogenous clock) is clearly established, the rats are given a daily administration of the compound to be tested.

The observations are made by means of visualisation of the rhythms of activity:
  influence of the light rhythm on the rhythms of activity,
  disappearance of the influence on the rhythms in permanent darkness.
  influence by the daily administration of the compound; transitory or durable effect.
A software package makes it possible:
  to measure the duration and intensity of the activity, the period of the rhythm of the animals during free course and during treatment,
  possibly to demonstrate by spectral analysis the existence of circadian and non-circadian (for example ultradian) components.

Results

The compounds of the invention clearly appear to have a powerful action on the circadian rhythm via the melatoninergic system.

EXAMPLE E

Illuminated/Darkened Cages Test

The compounds of the invention are tested on a behavioural model, the illuminated/darkened cages test, which enables the anxiolytic activity of the compounds to be revealed.

The equipment comprises two polyvinyl boxes covered with Plexiglas. One of the boxes is in darkness. A lamp is placed above the other box, yielding a light intensity of approximately 4000 lux at the centre of the box. An opaque plastic tunnel separates the illuminated box from the dark box. The animals are tested individually for a session of 5 minutes. The floor of each box is cleaned between each session. At the start of each test, the mouse is placed in the tunnel, facing the darkened box. The time spent by the mouse in the illuminated box and the number of passages through the tunnel are recorded after the first entry into the darkened box.

After administration of the compounds 30 minutes before the start of the test, the compounds of the invention significantly increase the time spent in the illuminated cage and the number of passages through the tunnel, which demonstrates the anxiolytic activity of the compounds of the invention.

EXAMPLE F

Activity of the Compounds of the Invention on the Caudal Artery of the Rat

The compounds of the invention were tested in vitro on the caudal artery of the rat. Melatoninergic receptors are present in those vessels, thus providing a relevant pharmacological model for studying melatoninergic ligand activity. The stimulation of the receptors can induce either vasoconstriction or dilation depending upon the arterial segment studied.

Protocol

One-month-old rats are accustomed to a light/dark cycle of 12 h/12 h during a period of 2 to 3 weeks.

After sacrifice, the caudal artery is isolated and maintained in a highly oxygenated medium. The arteries are then cannulated at both ends, suspended vertically in an organ chamber in a suitable medium and perfused via their proximal end. The pressure changes in the perfusion flow enable evaluation of the vasoconstrictive or vasodilatory effect of the compounds.

The activity of the compounds is evaluated on segments that have been pre-contracted by phenylephrine (1 μM). A concentration/response curve is determined non-cumulatively by the addition of a concentration of the test compound to the pre-contracted segment. When the effect observed reaches equilibrium, the medium is changed and the preparation is left for 20 minutes before the addition of the same concentration of phenylephrine and a further concentration of the test compound.

Results

The compounds of the invention significantly modify the diameter of caudal arteries pre-constricted by phenylephrine.

EXAMPLE G

Pharmaceutical Composition: Tablets

| | |
|---|---|
| 1000 tablets containing a dose of 5 mg of N-[2-(2-methoxy-6H-pyrido[2',3':4,5]pyrrolo-[2,1-α]isoindol-11-yl)ethyl]-2-furamide (Example 2) | 5 g |
| Wheat starch | 20 g |
| Maize starch | 20 g |
| Lactose | 30 g |
| Magnesium stearate | 2 g |
| Silica | 1 g |
| Hydroxypropylcellulose | 2 g |

We claim:

1. A compound selected from those of formula (I):

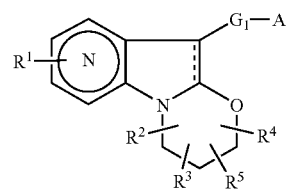

wherein:

the symbol

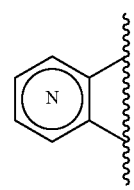

represents

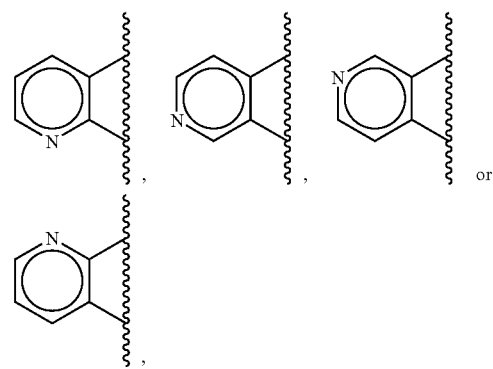

$R^1$ represents halogen or —R, —OR, —S(O)$_n$R, —NRR',

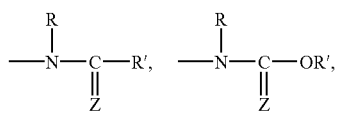

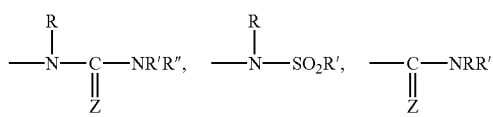

or —SO$_2$NRR' wherein n is 0, 1 or 2, Z represents sulphur or oxygen, and R, R' and R", which may be identical or different, represent hydrogen or unsubstituted or substituted linear or branched (C$_1$-C$_6$)alkyl, unsubstituted or substituted linear or branched (C$_2$-C$_6$) alkenyl, unsubstituted or substituted linear or branched (C$_2$-C$_6$)alkynyl, unsubstituted or substituted (C$_3$-C$_8$) cyclo-alkyl, unsubstituted or substituted (C$_3$-C$_8$)cycloalkyl-(C$_1$-C$_6$)alkyl in which the alkyl moiety is linear or branched, aryl, aryl-(C$_1$-C$_6$)alkyl in which the alkyl moiety is linear or branched, heteroaryl or heteroaryl-(C$_1$-C$_6$)alkyl in which the alkyl moiety is linear or branched, it also being possible for (R and R') and (R' and R"), when either (R and R') and/or (R' and R") are attached to the same nitrogen atom, to form together with the nitrogen atom carrying them morpholinyl, piperidinyl, piperazinyl or pyrrolidinyl, those groups being unsubstituted or substituted, G$_1$ represents an alkylene chain having from 1 to 4 carbon atoms, optionally substituted by R, OR, COR or COOR wherein R is as defined hereinbefore, or G$_1$ represents an alkylene chain having from 1 to 4 carbon atoms in which one of the CH$_2$ groups can be replaced by a cycloalkylene (C$_3$-C$_8$), A represents

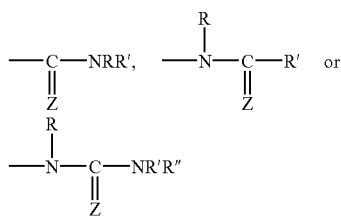

wherein R, R', R" and Z are as defined hereinbefore,
R$^2$ and R$^3$, which may be identical or different, represent hydrogen or linear or branched (C$_1$-C$_6$)alkyl, linear or branched (C$_1$-C$_6$)alkoxy or hydroxy,
or R$^2$ and R$^3$ together form oxo,
R$^4$ and R$^5$ represent hydrogen,
the symbol ----- means that the bond may be single or double, with the proviso that the valence of the atoms is respected,
it being understood that:
the term "substituted" applied to the terms "alkyl", "alkenyl", "alkynyl", "cycloalkyl", "morpholinyl", "piperidinyl", "piperazinyl" and "pyrrolidinyl" means that those groups may be substituted by one or more groups selected from hydroxy, oxo, alkoxy, alkyl, polyhaloalkyl, and halogen,
the term "substituted" applied to the term "cycloalkylalkyl" means that the cyclic moiety of the group is substituted by one or more groups selected from hydroxy, oxo, alkoxy, alkyl, polyhaloalkyl, and halogen,
"aryl" is understood to mean phenyl, naphthyl or biphenyl, those groups being unsubstituted or substituted by one or more identical or different groups selected from hydroxy, alkoxy, alkyl, amino, alkylamino, dialkylamino, nitro, cyano, polyhaloalkyl, formyl, carboxy, alkoxycarbonyl, amido, and halogen,
"heteroaryl" is understood to mean furyl, pyrrolyl, imidazolyl, pyridyl, thienyl, pyrazinyl, benzothienyl, benzofuranyl, indolyl, benzimidazolyl, quinolyl or quinazolinyl, those groups being unsubstituted or substituted by one or more identical or different groups selected from hydroxy, alkoxy, alkyl, amino, alkylamino, dialkylamino, nitro, cyano, polyhaloalkyl, formyl, carboxy, amido, and halogen,
its enantiomers and diastereoisomers, and addition salts thereof with a pharmaceutically acceptable acid or base.

2. A compound selected from those of formula (I):

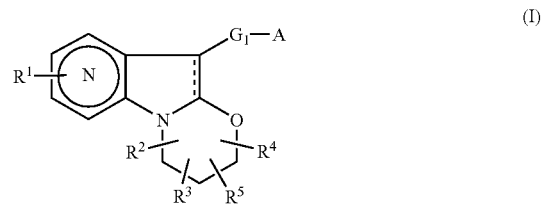

wherein:
the symbol

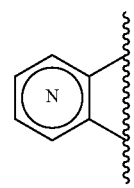

represents

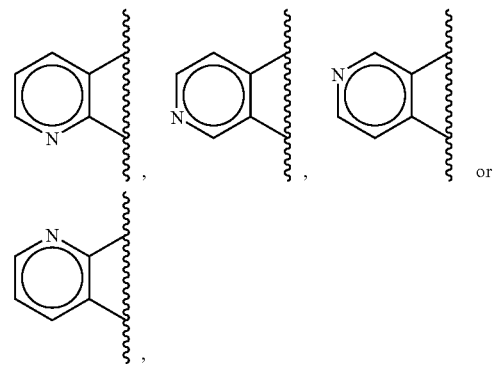

$R^1$ represents halogen or —R, —OR, —S(O)$_n$R, —NRR',

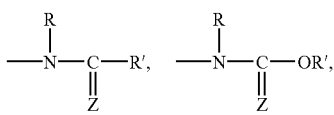

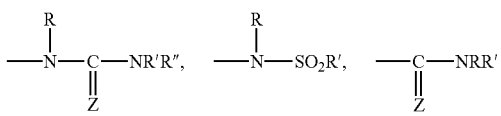

or —SO$_2$NRR' wherein n is 0, 1 or 2, Z represents sulphur or oxygen, and R, R' and R", which may be identical or different, represent hydrogen or unsubstituted or substituted linear or branched (C$_1$-C$_6$)alkyl, unsubstituted or substituted linear or branched (C$_2$-C$_6$)alkenyl, unsubstituted or substituted linear or branched (C$_2$-C$_6$)alkynyl, unsubstituted or substituted (C$_3$-C$_8$)cyclo-alkyl, unsubstituted or substituted (C$_3$-C$_8$)cycloalkyl-(C$_1$-C$_6$)alkyl in which the alkyl moiety is linear or branched, aryl, aryl-(C$_1$-C$_6$)alkyl in which the alkyl moiety is linear or branched, heteroaryl or heteroaryl-(C$_1$-C$_6$)alkyl in which the alkyl moiety is linear or branched, it also being possible for (R and R') and (R' and R"), when either (R and R') and/or (R' and R") are attached to the same nitrogen atom, to form together with the nitrogen atom carrying them morpholinyl, piperidinyl, piperazinyl or pyrrolidinyl, those groups being unsubstituted or substituted, $G_1$ represents an alkylene chain having from 1 to 4 carbon atoms, optionally substituted by R, OR, COR or COOR wherein R is as defined hereinbefore, A represents

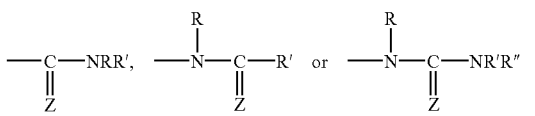

wherein R, R', R" and Z are as defined hereinbefore, $R^2$ and $R^3$, which may be identical or different, represent hydrogen or linear or branched (C$_1$-C$_6$)alkyl, linear or branched (C$_1$-C$_6$)alkoxy or hydroxy, or $R^2$ and $R^3$ together form oxo, $R^4$ and $R^5$ represent hydrogen, the symbol ----means that the bond may be single or double, with the proviso that the valence of the atoms is respected, it being understood that:
the term "substituted" applied to the terms "alkyl", "alkenyl", "alkynyl", "cycloalkyl", "morpholinyl", "piperidinyl", "piperazinyl" and "pyrrolidinyl" means that those groups may be substituted by one or more groups selected from hydroxy, oxo, alkoxy, alkyl, polyhaloalkyl, and halogen, the term "substituted" applied to the term "cycloalkylalkyl" means that the cyclic moiety of the group is substituted by one or more groups selected from hydroxy, oxo, alkoxy, alkyl, polyhaloalkyl, and halogen, "aryl" is understood to mean phenyl, naphthyl or biphenyl, those groups being unsubstituted or substituted by one or more identical or different groups selected from hydroxy, alkoxy, alkyl, amino, alkylamino, dialkylamino, nitro, cyano, polyhaloalkyl, formyl, carboxy, alkoxycarbonyl, amido, and halogen, "heteroaryl" is understood to mean furyl, pyrrolyl, imidazolyl, pyridyl, thienyl, pyrazinyl, benzothienyl, benzofuranyl, indolyl, benzimidazolyl, quinolyl or quinazolinyl, those groups being unsubstituted or substituted by one or more identical or different groups selected from hydroxy, alkoxy, alkyl, amino, alkylamino, dialkylamino, nitro, cyano, polyhaloalkyl, formyl, carboxy, amido, and halogen, its enantiomers and diastereoisomers, and addition salts thereof with a pharmaceutically acceptable acid or base.

3. A compound selected from those of formula (I):

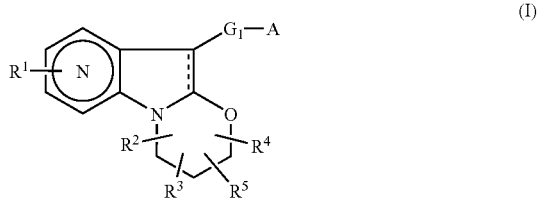

wherein:
the symbol

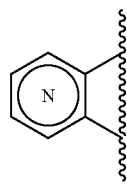

represents

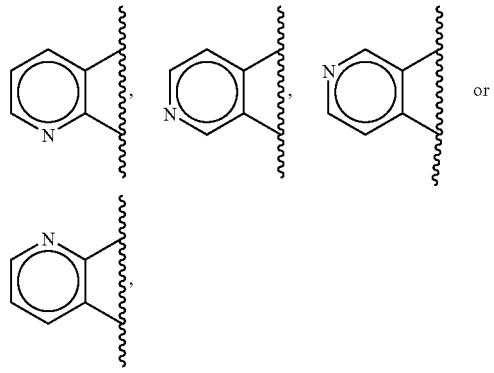

$R^1$ represents halogen or —R, —OR, —S(O)$_n$R, —NRR',

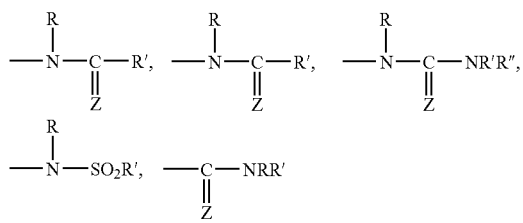

or —SO$_2$NRR' wherein n is 0, 1 or 2, Z represents sulphur or oxygen, and R, R' and R", which may be identical or different, represent hydrogen or unsubstituted or substituted linear or branched (C$_1$-C$_6$)alkyl, unsubstituted or substituted linear or branched (C$_2$-C$_6$) alkenyl, unsubstituted or substituted linear or branched (C$_2$-C$_6$)alkynyl, unsubstituted or substituted (C$_3$-C$_8$) cyclo-alkyl, unsubstituted or substituted (C$_3$-C$_8$)cycloalkyl-(C$_1$-C$_6$)alkyl in which the alkyl moiety is linear or branched, aryl, aryl-(C$_1$-C$_6$)alkyl in which the alkyl moiety is linear or branched, heteroaryl or heteroaryl-(C$_1$-C$_6$)alkyl in which the alkyl moiety is linear or branched, it also being possible for (R and R') and (R' and R"), when either (R and R') and/or (R' and R") are attached to the same nitrogen atom, to form together with the nitrogen atom carrying them morpholinyl, piperidinyl, piperazinyl or pyrrolidinyl, those groups being unsubstituted or substituted, G$_1$ represents an alkylene chain having from 1 to 4 carbons atoms in which one of the CH$_2$ groups can be replaced by a cycloalkylene (C$_3$-C$_8$),

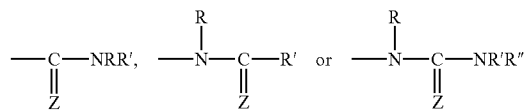

A represents
wherein R, R', R" and Z are as defined hereinbefore,
R$^2$ and R$^3$, which may be identical or different, represent hydrogen or linear or branched (C$_1$-C$_6$)alkyl, linear or branched (C$_1$-C$_6$)alkoxy or hydroxy,
or R$^2$ and R$^3$ together form oxo,
R$^4$ and R$^5$ represent hydrogen,
the symbol ----- means that the bond may be single or double, with the proviso that the valence of the atoms is respected, it being understood that:
the term "substituted" applied to the terms "alkyl", "alkenyl", "alkynyl", "cycloalkyl", "morpholinyl", "piperidinyl", "piperazinyl" and "pyrrolidinyl" means that those groups may be substituted by one or more groups selected from hydroxy, oxo, alkoxy, alkyl, polyhaloalkyl, and halogen, the term "substituted" applied to the term "cycloalkylalkyl" means that the cyclic moiety of the group is substituted by one or more groups selected from hydroxy, oxo, alkoxy, alkyl, polyhaloalkyl, and halogen, "aryl" is understood to mean phenyl, naphthyl or biphenyl, those groups being unsubstituted or substituted by one or more identical or different groups selected from hydroxy, alkoxy, alkyl, amino, alkylamino, dialkylamino, nitro, cyano, polyhaloalkyl, formyl, carboxy, alkoxycarbonyl, amido, and halogen, "heteroaryl" is understood to mean furyl, pyrrolyl, imidazolyl, pyridyl, thienyl, pyrazinyl, benzothienyl, benzofuranyl, indolyl, benzimidazolyl, quinolyl or quinazolinyl, those groups being unsubstituted or substituted by one or more identical or different groups selected from hydroxy, alkoxy, alkyl, amino, alkylamino, dialkylamino, nitro, cyano, polyhaloalkyl, formyl, carboxy, amido, and halogen, its enantiomers and diastereoisomers, and addition salts thereof with a pharmaceutically-acceptable acid or base.

4. A compound according to claim 1 wherein R$^2$, R$^3$, R$^4$ and R$^5$ simultaneously represent hydrogen.

5. A compound according to claim 1 wherein R$^1$ represents OR.

6. A compound according to claim 1 wherein G$_1$ represents —CH$_2$CH$_2$— or —CH$_2$CH$_2$CH$_2$—.

7. A compound according to claim 1 wherein A represents NHCOR.

8. A compound according to claim 1 wherein A represents CONHR.

9. A compound according to claim 1 which is selected from N-[2-(8-methoxy-3,4-dihydro-2H-pyrido[2',3':4,5]pyrrolo[2,1-b][1,3]oxazin-10-yl)ethyl]acetamide, N-[2-(8-methoxy-3,4-dihydro-2H-pyrido[2',3':4,5]pyrrolo[2,1-b][1,3]oxazin-10-yl)ethyl]-2-furamide and addition salts thereof with a pharmaceutically-acceptable acid or base.

10. A method for treating a living animal body, including a human, afflicted with a condition selected from anxiety and insomnia, comprising the step of administering to the living animal body, including a human, an amount of a compound of claim 1 which is effective for alleviation of the condition.

11. A pharmaceutical composition comprising as active principle an effective amount of a compound of claim 1, together with one or more pharmaceutically-acceptable excipients or vehicles.

* * * * *

UNITED STATES PATENT AND TRADEMARK OFFICE
CERTIFICATE OF CORRECTION

PATENT NO.       : 7,235,550 B2
APPLICATION NO.  : 10/267303
DATED            : June 26, 2007
INVENTOR(S)      : Gerald Guillaumet et al.

It is certified that error appears in the above-identified patent and that said Letters Patent is hereby corrected as shown below:

Column 43 Lines 3-10:

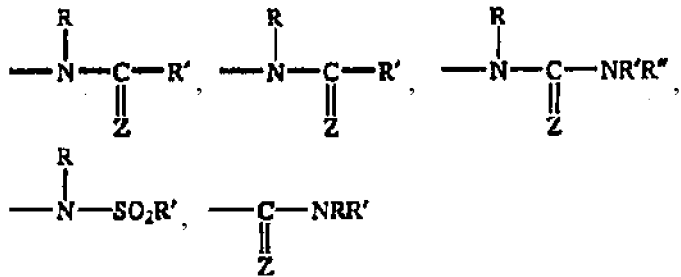

Should be

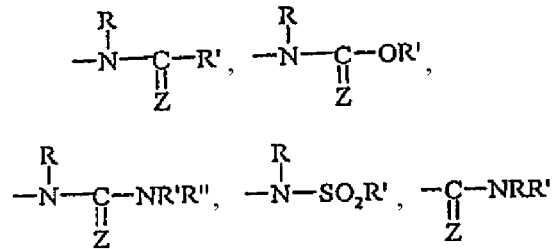

Column 43, Line 37-46

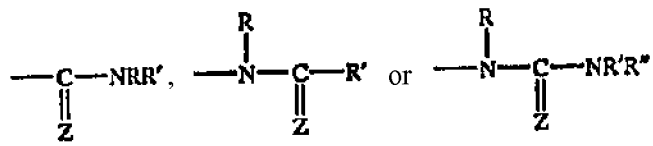

A represents

UNITED STATES PATENT AND TRADEMARK OFFICE
CERTIFICATE OF CORRECTION

PATENT NO.       : 7,235,550 B2
APPLICATION NO.  : 10/267303
DATED            : June 26, 2007
INVENTOR(S)      : Gerald Guillaumet et al.

It is certified that error appears in the above-identified patent and that said Letters Patent is hereby corrected as shown below:

Column 43, Line 37-46 (cont'd)

Should be

A represents

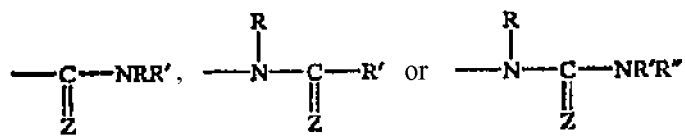

Signed and Sealed this

Twentieth Day of November, 2007

JON W. DUDAS
*Director of the United States Patent and Trademark Office*